(12) United States Patent
Inagaki

(10) Patent No.: US 10,271,792 B2
(45) Date of Patent: Apr. 30, 2019

(54) BIOLOGICAL INFORMATION MEASURING APPARATUS

(71) Applicant: SEIKO EPSON CORPORATION, Tokyo (JP)

(72) Inventor: Akira Inagaki, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 727 days.

(21) Appl. No.: 14/946,621

(22) Filed: Nov. 19, 2015

(65) Prior Publication Data

US 2016/0143584 A1 May 26, 2016

(30) Foreign Application Priority Data

Nov. 20, 2014 (JP) .................. 2014-235329

(51) Int. Cl.
*A61B 5/00* (2006.01)
*A61B 5/024* (2006.01)

(52) U.S. Cl.
CPC .......... *A61B 5/681* (2013.01); *A61B 5/02416* (2013.01); *A61B 5/02438* (2013.01); *A61B 5/002* (2013.01); *A61B 5/721* (2013.01); *A61B 2562/0219* (2013.01); *A61B 2562/164* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,742,256 A | * | 4/1998 | Wakabayashi | H01Q 1/273 224/178 |
| 2010/0323154 A1 | * | 12/2010 | Sharobiem | A44C 5/00 428/131 |
| 2013/0261405 A1 | * | 10/2013 | Lee | A61B 5/681 600/301 |

FOREIGN PATENT DOCUMENTS

| | | | |
|---|---|---|---|
| JP | S59-111515 U | 7/1984 | |
| JP | H8-154712 | 6/1996 | |
| JP | H10-005014 A | 1/1998 | |
| JP | 2006-271610 A | 10/2006 | |
| JP | 2007-178757 A | 7/2007 | |
| JP | 2007178757 A * | 7/2007 | ............. G09F 3/005 |
| JP | 2008-168054 A | 7/2008 | |
| JP | 2010-110634 A | 5/2010 | |

* cited by examiner

*Primary Examiner* — Scott T Luan
(74) *Attorney, Agent, or Firm* — Maschoff Brennan

(57) ABSTRACT

A biological information measuring apparatus (measuring apparatus) includes a band which fixes a case unit to a living body. The band is provided with a recessed groove part on a side facing the living body. The groove part has a depth of 1020 μm or more and 1140 μm or less.

17 Claims, 15 Drawing Sheets

BIOLOGICAL INFORMATION MEASURING APPARATUS

This application claims priority to Japanese Patent Application No. 2014-235329, filed Nov. 20, 2014, the entirety of which is hereby incorporated by reference.

BACKGROUND

1. Technical Field

The present invention relates to a biological information measuring apparatus.

2. Related Art

According to the related art, a measuring apparatus which is installed at a site such as the wrist with a band or the like and measures biological information such as the pulse waves and pulse rates of the wearer, and a wristwatch-like electronic apparatus having the function of measuring such biological information, are known (see, for example, JP-A-2010-110634 and JP-A-2006-271610). In the case of such apparatuses (measuring apparatus and electronic apparatus), a case unit (main body unit) having a display unit is installed on the wrist with two bands extending on both sides of the case unit. On the back side of the case unit (opposite side of the display unit), a detection unit (sensor) for optically detecting pulse waves is arranged.

In such apparatuses, the detection unit needs to be in tight contact with the arm in order to measure biological information stably. More specifically, the apparatus needs to be wearable in the state where the case unit is in tight contact with the site where the apparatus is installed, for example, the wrist, even if the circumferential size or cross-sectional shape of the site differs from wearer to wearer. Also, in order to continue measuring biological information, the whole apparatus including the bands needs to have a small-sized and lightweight configuration so that the wearer can wear the apparatus comfortably for a longtime with little burden.

To cope with this need, JP-A-2010-110634 discloses a configuration in which each of the two bands extending on both sides of the case unit (device main body) is provided with an expansion/contraction part capable of expanding and contracting in the longitudinal direction of the band. According to this, the detection unit can be brought in tight contact with the arm by the restoring force in the expansion and contraction of the expansion/contraction part. JP-A-2006-271610 discloses a configuration in which one band (band piece) is made up of two band members, with the two band members connected together via a connection member with high expansion/contraction ability. According to this, the detection unit can be brought in tight contact with the arm by the restoring force in the expansion and contraction of the connection member.

In such related-art apparatuses, as the detection unit (sensor) is brought in tight contact with the wrist, the bands are brought in tight contact with the wrist as well. Therefore, if the apparatus is worn on the wrist for a long time, the wearer's sweat and inevitable moisture in living (for example, drops of water after washing the hands) accumulate between the bands and the skin, causing the problem of discomfort experienced by the wearer.

To cope with this problem, it is effective to provide a groove on the surface of the bands that contacts the wrist, for example, so as to reduce the contact area between the bands and the skin or to release the sweat and moisture outside. In each of JP-A-2010-110634 and JP-A-2006-271610, FIG. 1 shows a groove-like site extending in the longitudinal direction of the band, in a center part on the surface of the band that contacts the wrist. However, the shape of the groove-like site, including the depth dimension, length dimension or width dimension, is not described in the text at all.

However, in the related-art apparatuses, if the groove shape is not properly set, there is a risk that the sweat and moisture cannot be released outside sufficiently or that the strength (durability) of the bands may not be sufficient.

Specifically, if the width of the groove is too narrow or the depth of the groove is too shallow, it is difficult for the sweat and moisture to escape outside from the tight contact part between the bands and the skin, and consequently the sweat and moisture remaining in the tight contact part between the bands and the skin cause discomfort to the wearer. In other words, the sensation of wearing experienced by the wearer is impaired and the wearer ends up feeling stressed about long-time wearing. In some cases, the wearer may give up wearing the apparatus. If the wearer gives up wearing the apparatus in this way, biological information (health state) such as the pulse waves of the wearer can no longer be measured (grasped). Also, if the width of the groove is narrow or the depth of the groove is shallow, the flexibility of the bands is impaired. Therefore, the durability with time of the bands may fall and damage such as cracking may occur.

Meanwhile, if the width of the groove is too broad or the depth of the groove is too deep, the strength of the bands falls, leading to damage to the bands, or deformation of the bands due to an impact or acceleration (G) applied to the apparatus at the time of running, for example. Therefore, the tight contactability between the detection unit (sensor) and the skin may fall. Consequently, biological information (health state) such as the pulse waves of the wearer can no longer be measured (grasped) accurately.

SUMMARY

An advantage of some aspects of the invention is to solve at least a part of the problems described above, and the invention can be implemented as the following forms or application examples.

Application Example 1

A biological information measuring apparatus according to this application example includes: a detection unit which detects biological information; a case unit which houses the detection unit; and a band which fixes the case unit to a living body. The band is provided with a recessed groove part on a side facing the living body. The groove part has a depth of 1020 μm or more and 1140 μm or less.

According to this application example, since the depth of the groove part provided on the side of the band facing the living body is 1020 μm or more and 1140 μm or less, the sweat and moisture can be sufficiently released outside without lowering the strength (durability) of the band. In other words, inaccurate measurement (grasping) of biological information (health state) such as the pulse waves of the wearer due to a fall in the tight contactability between the detection unit (sensor) and the living body (skin) caused by deformation or the like of the band can be prevented, without spoiling the sensation of wearing experienced by the wearer.

Application Example 2

In the biological information measuring apparatus, it is preferable that the depth of the groove part is 1050 μm or more and 1100 or less.

According to this application example, since the depth of the groove part is 1050 μm or more and 1100 μm or less, ventilation in the groove part is improved, enabling the sweat and moisture to be released outside sufficiently.

Application Example 3

In the biological information measuring apparatus, it is preferable that the depth of the groove part is 1060 μm or more and 1080 μm or less.

According to this application example, since the depth of the groove part is 1060 μm or more and 1080 μm or less, ventilation in the groove part is improved further, enabling the sweat and moisture to be released outside sufficiently. Also, the flexibility of the band increases, enabling improvement in the sensation of fitting (sensation of wearing) with the wearing part (living body).

Application Example 4

In the biological information measuring apparatus, it is preferable that the depth of the groove part at an end of the band is deeper than the depth of the groove part in the other parts of band.

According to this application example, since the end of the band has a large opening area, ventilation can be improved further, making it easier to release the sweat and moisture outside.

Application Example 5

A biological information measuring apparatus according to this application example includes: a detection unit which detects biological information; a case unit which houses the detection unit; and a band which fixes the case unit to a living body. The band is provided with a recessed groove part on a side facing the living body. The groove part has a width of 910 μm or more and 2300 μm or less.

According to this application example, the sweat and moisture can be sufficiently released outside without lowering the strength (durability) of the band. In other words, inaccurate measurement (grasping) of biological information (health state) such as the pulse waves of the wearer due to a fall in the tight contactability between the detection unit (sensor) and the living body (skin) caused by deformation or the like of the band can be prevented, without impairing the sensation of wearing experienced by the wearer.

Application Example 6

In the biological information measuring apparatus, it is preferable that the width of the groove part is 950 μm or more and 2000 μm or less.

According to this application example, since the width of the groove part is 950 μm or more and 2000 μm or less, the strength of the band can be increased further while ventilation in the groove part is secured.

Application Example 7

In the biological information measuring apparatus, it is preferable that the width of the groove part is 1000 μm or more and 1700 μm or less.

According to this application example, since the groove part with a width of 1000 μm or more and 1700 μm or less is provided, the width of a bank-like wall part (contact part with the wearing part (living body) of the wearer) formed on the band by the provision of the groove part can be increased. Therefore, biting into the wearing part (living body) of the wearer by the bank-like wall part can be reduced and the sensation of wearing experienced by the wearer can be prevented from being spoiled. Thus, the sensation of wearing experienced by the wearer, including sufficiently releasing the sweat and moisture outside, can be improved and a fall in the strength (durability) of the band can be prevented.

Application Example 8

In the biological information measuring apparatus, it is preferable that the width of the groove part at an end of the band is broader than the width of the groove part in the other parts of the band.

According to this application example, since the end of the band has a large opening area, ventilation can be improved further, making it easier to release the sweat and moisture outside.

Application Example 9

In the biological information measuring apparatus, it is preferable that the groove part is provided along a direction of extension of the band.

According to this application example, the sweat and moisture generated in the band can be released outside from the groove part.

Application Example 10

In the biological information measuring apparatus, it is preferable that the groove part is provided to reach the case unit.

According to this application example, the sweat and moisture generated in the case part addition to the band can be released outside from the groove part and the sensation of wearing can be improved further.

Application Example 11

In the biological information measuring apparatus, it is preferable that the groove part is provided along a direction intersecting with a direction of extension of the band.

According to this application example, in the case of installing the apparatus on a curved surface such as an arm part, the band can be easily deformed and the sensation of wearing (sensation of fitting) can be improved.

Application Example 12

In the biological information measuring apparatus, it is preferable that the band has a hole part penetrating the band from the side facing the living body to the opposite side, and that the groove part is provided to continue to the hole part.

According to this application example, since the sweat and moisture can also be released outside from the hole part continuing to the groove part, accumulation of the sweat and moisture in the wearing part (living body) of the wearer can be prevented and a more conformable sensation of wearing can be achieved.

Application Example 13

In the biological information measuring apparatus, it is preferable that the band includes a first band part extending on one side of the case unit, and a second band part extending on the opposite side via the case unit, and that the groove part is provided on the first band part and the second band part.

According to this application example, since the band includes the first band part and the second band part via the case unit, the detection unit can be easily brought in tight contact with the wearing part (living body) without spoiling the sensation of wearing. Also, since the groove part is provided in the first band part and the second band part, sweat and moisture can be released from the entire band.

Application Example 14

In the biological information measuring apparatus, it is preferable that the band is made of a material that is deformable along the living body.

According to this application example, since the band is made of a material that is deformable along the living body, the case unit can be fixed to the arm with a proper pressurizing force while ventilation through the groove part is secured. Thus, the detection unit can be brought in tight contact with a detection position.

Application Example 15

In the biological information measuring apparatus, it is preferable that the band is made of an elastic resin material.

According to this application example, since the band is made of an elastic resin, the case unit can be fixed to the arm with a proper pressurizing force while ventilation through the groove part is secured. Thus, the detection unit can be brought in tight contact with the wearing part (living body).

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1A:
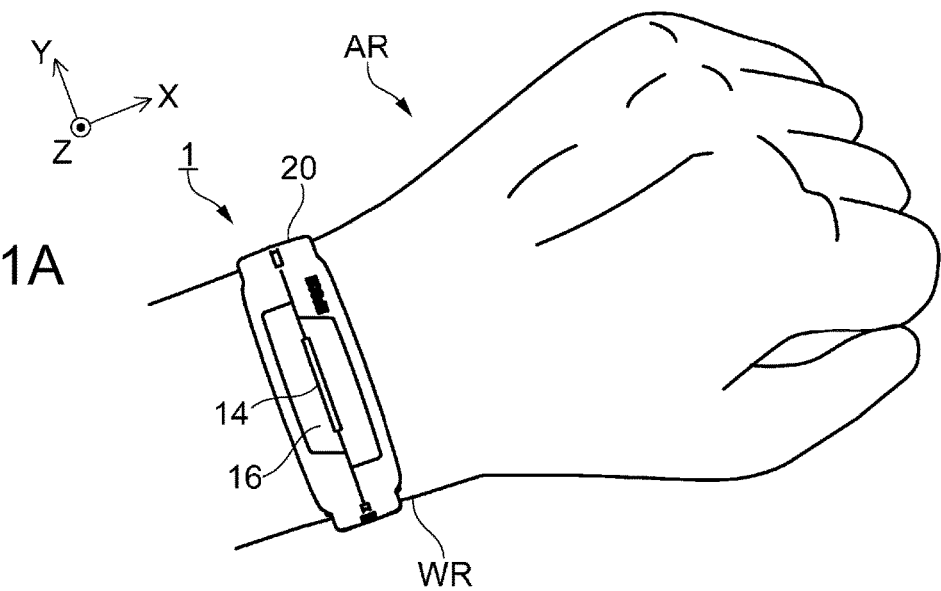
FIGS. 1A and 1B are perspective views showing the schematic configuration of a biological information measuring apparatus according to Embodiment 1.

Hereinafter, embodiments of the invention will be described with reference to the drawings. In the drawings below, each layer or part is shown in a size that can be recognized in the illustrations and is different from the actual scale of each layer or part.

Embodiment 1

Outline of Biological Information Measuring Apparatus

Figure 1B:
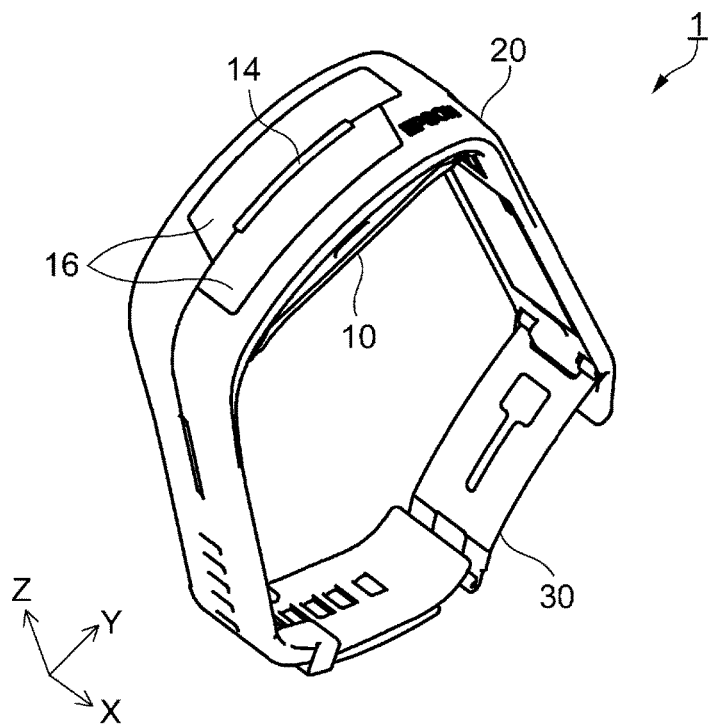

FIGS. 1A and 1B show the schematic configuration of a biological information measuring apparatus according to Embodiment 1. FIG. 1A shows a wearing state where the biological information measuring apparatus is installed on a living body. FIG. 1B shows an open state where the biological information measuring apparatus is removed from the living body.

A biological information measuring apparatus (hereinafter also referred to as a measuring apparatus) 1 according to this Embodiment 1 is an electronic apparatus which is installed on a living body (for example, a human body) whose biological information is measured, and which measures biological information such as pulse waves. As shown in FIG. 1A, the measuring apparatus 1 is installed at a measuring site (wrist or the like) of the wearer (living body) like a wristwatch and used in this state. In the embodiment, the state where the measuring apparatus 1 is installed on the wrist WR of the left arm AR of the wearer is shown.

In this specification, the direction of a normal line to a front of the measuring apparatus 1 is defined as a Z-axis direction, in which the forward side in FIG. 1A is positive. The front of the measuring apparatus 1 refers to the side where a light emitting unit 14 is arranged. A direction which intersects with the Z-axis direction and along the direction of length of the arm AR is defined as an X-axis direction, in which the distal end side where the fingers are situated is positive. A direction which intersects with the Z-axis direction and the X-axis direction and along the direction of the width of the arm AR is defined as a Y-axis direction, in which the little finger side is positive.

In the specification, viewing the measuring apparatus 1 from the direction of a normal line to the front (Z-axis direction) is referred to as "in a front view". Viewing the measuring apparatus 1 from the X-axis direction is referred to as "in a side view". In the state where the measuring apparatus 1 is installed on the wrist WR, the living body side, that is, the side facing the wrist WR, is called an "inner side" or "inner surface". The side opposite to the living body, that is, the opposite side of the side facing the wrist WR, is called an "outer side" or "outer surface".

The measuring apparatus 1 does not have a monitor unit (display) for displaying letters, graphics and the like, unlike a general biological information measuring apparatus (hereinafter referred to as a general measuring apparatus) similar to a wristwatch. Instead, the measuring apparatus 1 has the light emitting unit 14. The measuring apparatus 1 does not have buttons and switches for operating, unlike a general measuring apparatus. The measuring apparatus 1 measures biological information in the state where a bottom surface (detection unit) on the side opposite to the front of the measuring apparatus 1 is in tight contact with the wrist WR. Also, an oscillation motor and alarm or the like may be used instead of the light emitting unit 14.

As shown in FIG. 1B, the measuring apparatus 1 has a case unit 10 which is an apparatus main body, a band 20 which fixes the case unit 10 to the wrist WR, and a buckle part 30 connecting to the band 20.

The band 20 covers the front side of the case unit 10 along the Y-axis direction. Also, the band 20 extends from both sides of the case unit 10 and is connected by the buckle part 30.

The buckle part 30 is a hinge-like member made up of two metallic plates connected via a swivel axis. The buckle part 30 is structured in such a way that when the two plates are folded on top of each other, the length of the buckle part 30 becomes shorter, whereas when the two plates are extended next to each other, the length of the buckle part 30 becomes longer.

That is, the measuring apparatus 1 includes the case unit 10 having a detection unit which detects biological information, the band 20 for fixing the case unit 10 to a living body, and the buckle part 30 which connects to the band 20 in a ring shape and whose length is adjustable.

As both ends of the band 20 are thus connected together via the buckle part 30, the measuring apparatus 1 is in a ring shape, both in the state of being installed on the wrist WR as shown in FIG. 1A (hereinafter referred to as a wearing state) and in the state of being removed from the wrist WR shown in FIG. 1B (hereinafter referred to as an open state).

With this configuration, when installing the measuring apparatus 1, the wearer leaves the buckle part 30 in an extended state, then inserts the pursed hand into the large ring-shaped opening shown in FIG. 1B, and then folds the buckle part 30 into a shorter length at the wearing position on the arm. Thus, the measuring apparatus 1 can be installed, as shown in FIG. 1A. Particularly, with various ingenious contrivances such as the optimization of the configuration, material, and the size of the ring-shaped opening, a configuration is realized that can fix the detection unit to the detection position on the arm accurately and with substantially equal pressurization (pressing force) even if the installation and removal of the measuring apparatus 1 are repeated. Details of the configuration will be described below.

Overall Configuration of Biological Information Measuring Apparatus

Figure 2:
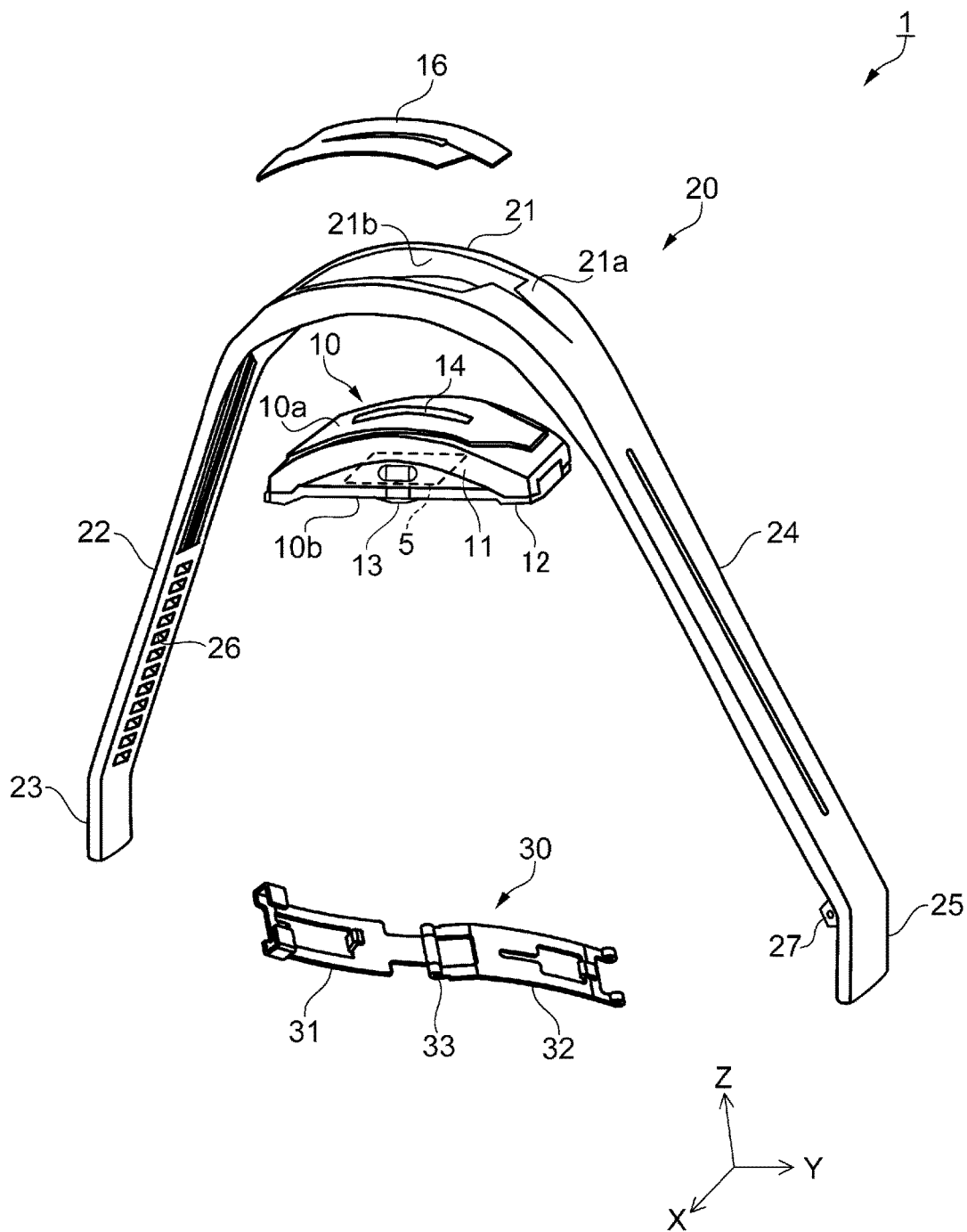
FIG. 2 is a developed view showing the schematic structure of the biological information measuring apparatus according to Embodiment 1.

FIG. 2 is a developed view showing the schematic structure of the biological information measuring apparatus.

As shown in FIG. 2, in the band 20, an opening 21b (hole part) is formed in the middle in the direction of extension of the band 20. The case unit 10, substantially rectangular as viewed in a plan view, is fitted in the opening 21b. The case unit 10 is fitted (inserted) in the opening 21b from the back side (side facing the wrist WR) of the band 20, with the light emitting unit 14 facing upward (to the front). The part where the opening 21b is formed in the direction of extension of the band 20 is formed to be broader than both ends.

The band 20 includes a first band part 22 extending toward one end from the opening 21b and a second band part 24 extending toward the other end. The band 20 in a single-piece (initial) state is in an inverted U-shape in which the first band part 22 and the second band part 24 hang down to the left and right from the middle (opening 21b) of the band 20 as the top, as viewed in a side view.

The case unit 10 includes a lateral part 11 along the Y-axis direction and an end part 12 along the X-axis direction, and is in a substantially rectangular shape in which the lateral part 11 forms the longer sides while the end part 12 forms the shorter side, as viewed in a front view. The case unit 10 has a top surface 10a made up of a convex curved surface on the front side of the measuring apparatus 1, and has a bottom surface 10b on the opposite side of the top surface 10a, that is, on the side facing the wrist WR. A window part 13 as a detection unit is arranged on the bottom surface 10b. A sensor which actually detects biological information is a photoelectric pulse wave sensor unit 5 arranged behind the window part 13. However, in terms of the structure, the site which protrudes most to the wrist WR side and needs tight contactability is the window part 13, and therefore the window part 13 is regarded as the detection unit. The case unit 10 is made of a resin material, for example, polycarbonate (PC), polystyrene (PS), ABS resin or the like.

The light emitting unit 14 is arranged on the top surface 10a of the case unit 10. The light emitting unit 14 includes a plurality of light emitting elements made up of LEDs (light emitting diodes) or the like, for example. In a preferred example, five LEDs are arranged in a line. The measuring apparatus 1 can notify the wearer of the operation mode of the measuring apparatus 1 and information related to the measurement of biological information, and the like, by varying the color of light emission of each light emitting element or by combining states such as switching on, switching off, and flashing on/off.

The band 20 extends along the Y-axis direction. A surface 21a of a main body part 21 of the band 20 is curved substantially arcuately along the top surface 10a of the case unit 10. It is preferable that the band 20 is made of a material that can be deformed along the living body in order to mount the measuring apparatus 1 on the living body (for example, the wrist WR of the arm AR of a human body) in such a way that the window part 13 as a detection unit (sensor) is brought in tight contact with the wrist WR, for example.

The material of the band 20 may be, for example, silicone rubber (silicone resin), natural rubber, rubber mixed with carbon black, isoprene rubber, butadiene rubber, styrene-butadiene rubber, chloroprene rubber, nitrile rubber, polyisobutylene, ethylene propylene rubber, chlorosulfonated polyethylene rubber, acrylic rubber, fluorine rubber, epichlorohydrin rubber, urethane rubber (urethane resin), polyurethane rubber (polyurethane resin), styrene-based elastomer, olefin-based elastomer, polyvinyl chloride-based elastomer, polyester-based elastomer, polyurethane-based elastomer, silicone-based elastomer, amide-based elastomer, nylon-based elastomer, dynamically cross-linked elastomer or the like, or mixtures of these. Other suitable materials may be synthetic skin, natural skin, natural leather, or various thermoplastic elastomers or the like such as polyethylene made from thermoplastic resin, polypropylene, polyolefin such as ethylene-vinyl acetate copolymer, modified polyolefin, polyamide (for example, nylon 6, nylon 46, nylon 66, nylon 610, nylon 612, nylon 11, nylon 12, nylon 6-12, nylon 6-66), thermoplastic polyimide, liquid-crystal polymer such as aromatic polyester, polyphenylene oxide, polyphenylene sulfide, polycarbonate, polymethyl methacrylate, polyether, polyether ether ketone, polyether imide, polyacetal, styrene group, polyolefin group, polyvinyl chloride group, polyurethane group, polyester group, polyamide group, polybutadiene group, trans-polyisoprene group, fluorine rubber group, chlorinated polyethylene group and the like, or copolymers, mixtures, polymer alloys or the like mainly containing these. One type of these, or a mixture of two or more types can be used. It is desirable that the band 20 has flexibility and elasticity that provide a proper tightening force to the wrist WR, and also has high durability and is gentle on the skin (little stimulating to the skin). As a material having such characteristics, silicone rubber can be used suitably.

As the band 20 is made of such materials, the case unit 10 can be fixed to the wrist WR with a proper pressurizing force while ventilation through groove parts 28, 29 described below (see FIG. 3C) is secured. Thus, the window part 13 as a detection unit (sensor) can be brought in tight contact with the detection position.

The band 20 includes the main body part 21 covering the top surface 10a of the case unit 10, the first band part 22 extending from the main body part 21 toward one side in a direction along the lateral part 11 of the case unit 10, and the second band part 24 extending from the main body part 21 toward the other side in the direction along the lateral part 11 of the case unit 10. The main body part 21, the first band part 22 and the second band part 24 are molded as a single body. The main body part 21 situated in the middle of the band 20 is curved along the top surface 10a of the case unit 10 and has the surface 21a which is made up of a convex curved surface. The opening 21b is formed in the main body part 21.

The first band part 22 and the second band part 24 extend in the way of warping toward the bottom surface 10b of the case unit 10 from the curved main body part 21. The first band part 22 has a distal end part 23 at the distal end thereof. The distal end part 23 is bent to the inner side from the direction of extension of the first band part 22. The second band part 24 has a distal end part 25 at the distal end thereof. The distal end part 25, too, is bent to the inner side from the second band part 24.

In the first band part 22, a plurality of adjustment hole parts 26 is provided, arrayed along the direction of extension of the first band part 22. The plurality of adjustment hole parts 26 is provided, penetrating the first band part 22 in the direction of the thickness thereof, and arranged at a substantially uniform pitch. The second band part 24 is provided with a connection part 27 on the side of the distal end part 25. The connection part 27 is provided, protruding in a convex form to the inner side from the second band part 24, and has a connection hole penetrating the connection part in the direction of the width of the second band part 24.

The buckle part 30 includes a first plate (first buckle part) 31, a second plate (second buckle part) 32, and a hinge part 33 axially supporting the first plate 31 and the second plate 32 to enable these plates to swivel. The buckle part 30 is a folding-type length adjustment member which connects the first band part 22 and the second band part 24 to each other. The first plate 31 is connected to the first band part 22. The second plate 32 is connected to the second band part 24. In a preferred example, stainless steel is mainly used as the material of the buckle part 30. However, this example is not limiting, and any material which has good corrosion resistance, satisfies folding durability and is lightweight may be used. For example, titanium may be used. Also, the buckle part 30 may be made of a resin instead of a metal. This increases the sense of unity between the band 20 and the buckle part 30 and therefore improves the appearance thereof.

The wearing state of the buckle part 30 is established as the second plate 32 is folded to be on top of the outside of the first plate 31. The open state of the buckle part 30 is established as the second plate 32 is moved away and unfolded from the first plate 31 to the outer side.

The case unit 10 and the band 20 are provided as a single body, with the top surface 10a side of the case unit 10 fitted in the opening 21b of the band 20. A part of the top surface 10a, the lateral part 11 and the end part 12 of the case unit 10 is covered with the band 20. Also, a part of the top surface 10a of the case unit 10 is covered with a cover part 16. The cover part 16 is a veneer having an opening at a part that is laid on top of the light emitting unit 14. The cover part 16 is made of a film member of a resin such as polycarbonate. The cover part 16 is colorfully colored and configured in such a way that letters or the like can be printed thereon. The cover part 16 protects the case unit 10 and also increases the degree of freedom in design.

The measuring apparatus 1 has a control unit, a power supply unit, a communication unit, a sensor unit and the like inside the case unit 10 as an apparatus main body. These components provided inside the case unit 10 are not shown in the drawings. The control unit is made up of, for example, a CPU, a ROM, a RAM and the like, and these hardware pieces and software stored in the ROM or the like collaborate to control the operation of the measuring apparatus 1. The power supply unit is made up of a power supply circuit, a battery and the like. A terminal part for recharging the battery is provided on the case unit 10.

The communication unit carries out wireless communications between the measuring apparatus 1 and an external apparatus such as a smartphone or personal computer on the basis of a known wireless communication method such as Bluetooth (trademark registered). Thus, it is possible to operate the measuring apparatus 1 from the external apparatus, or to transmit biological information measured by the measuring apparatus 1 to the external apparatus so as to store and manage the biological information of the wearer. The measuring apparatus 1 has the function of storing the measured biological information of the wearer and providing information such as the results of analysis of the biological information or whether the amount of exercise is proper or not, to the wearer on the basis of the stored information, in collaboration with the external apparatus.

As the sensor unit, a tap operation sensor unit (not shown) which detects a tap operation by the wearer is provided, in addition to the photoelectric pulse wave sensor unit 5 for detecting biological information. The photoelectric pulse wave sensor unit 5 includes a light emitting element such as an LED and a light receiving element such as a photodiode. The photoelectric pulse wave sensor unit 5 detects pulse waves of the wearer, by casting detection light from the light emitting elements toward the wrist WR of the wearer and then receiving, with the light receiving element, reflected light reflected from the blood vessels in the wrist WR. The detection light and the reflected light exit and become incident via the window part 13 as a detection unit. The measuring apparatus 1 measures the pulse rate of the wearer on the basis of the pulse waves detected by the photoelectric pulse wave sensor unit 5.

The tap operation sensor unit is made up of an acceleration sensor, for example. A tap operation is the operation of tapping the measuring apparatus 1 with a finger, palm or the like. The wearer performs the tap operation of tapping the measuring apparatus 1 and thereby operates the measuring apparatus 1. The measuring apparatus 1 detects the tap operation by the wearer on the basis of sensor information from the tap operation sensor unit. In the measuring apparatus 1, a simple operation is carried out with a tap operation, and various settings and detailed operations of the measuring apparatus 1 are carried out from the external apparatus via wireless communications. With this configuration, the measuring apparatus 1 needs no buttons or switches for operation. Also, a signal from the acceleration sensor can be used in the processing to restrain a body movement noise superimposed on a pulse wave signal at the time of detecting biological information.

The measuring apparatus 1 is an apparatus aimed at measuring biological information of the wearer in his or her everyday life, by being worn by the wearer not only at the time of exercising such as walking or running but constantly. To this end, it is demanded that the measuring apparatus 1 should cause little burden (for example, the weight, size and shape of the apparatus, and discomfort caused by the tightening force) on the wearer even if worn by the wearer for a long time, and should be able to measure biological information in a stable state regardless of the posture and action of the wearer. In the measuring apparatus 1, compared with a general measuring apparatus, miniaturization, lighter weight, and longer battery life are made possible by eliminating a monitor unit (display), buttons and switches. Also, in the case where the wearer measures the pulse rate at the time of exercise, a body movement noise caused by the exercise is superimposed on pulse waves detected by the detection unit. To extract only a pulse wave components from the pulse wave signal with the body movement noise superimposed thereon, an acceleration signal outputted from the acceleration sensor of the tap operation sensor unit may be utilized. Thus, a single acceleration sensor can be used both as the acceleration sensor for detecting a tap operation and as the acceleration sensor for extracting a pulse wave component, and therefore lower cost, miniaturization and longer battery life can be realized.

Configuration of Case Unit and Band

Figure 3A:
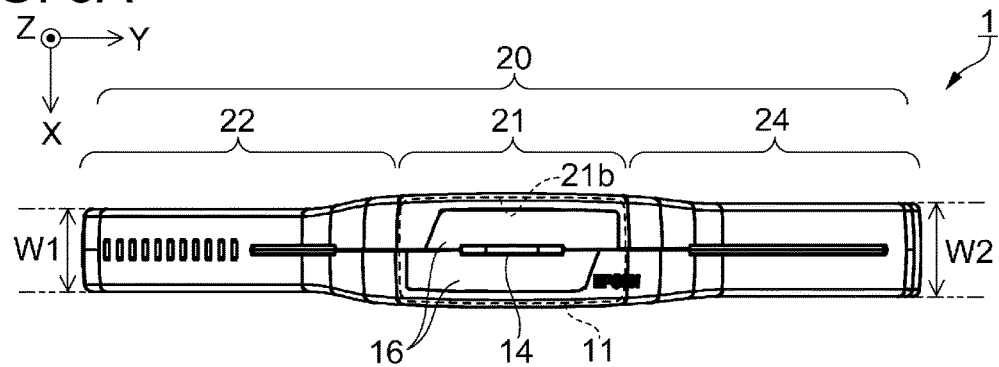
FIGS. 3A to 3C show the schematic configuration of a case unit and a band according to Embodiment 1.
Figure 3B:
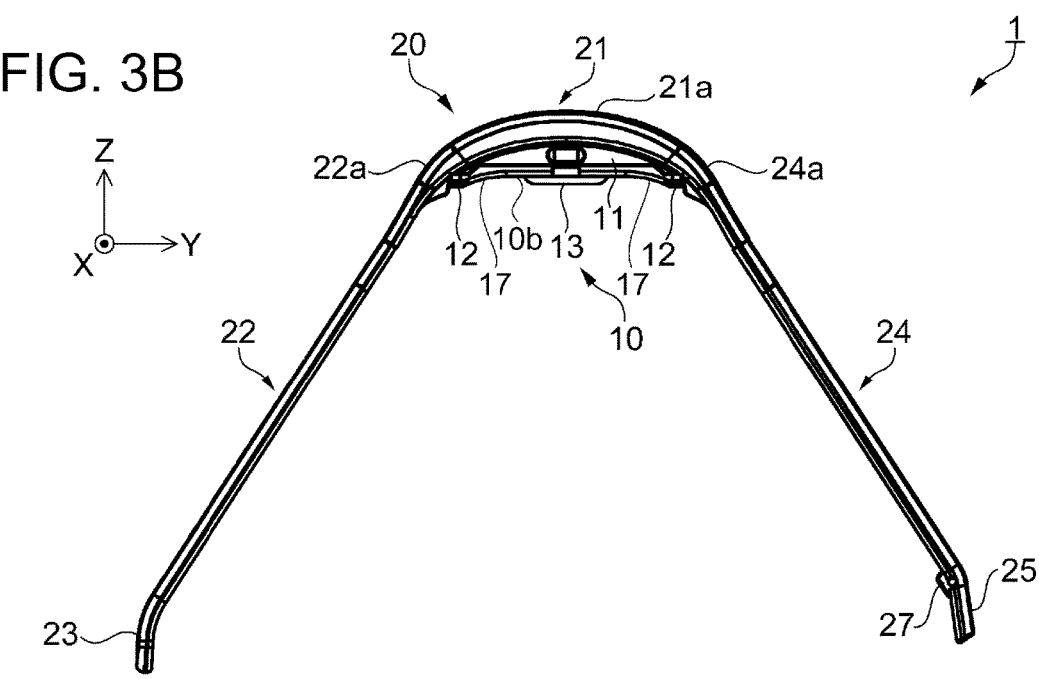
Figure 3C:
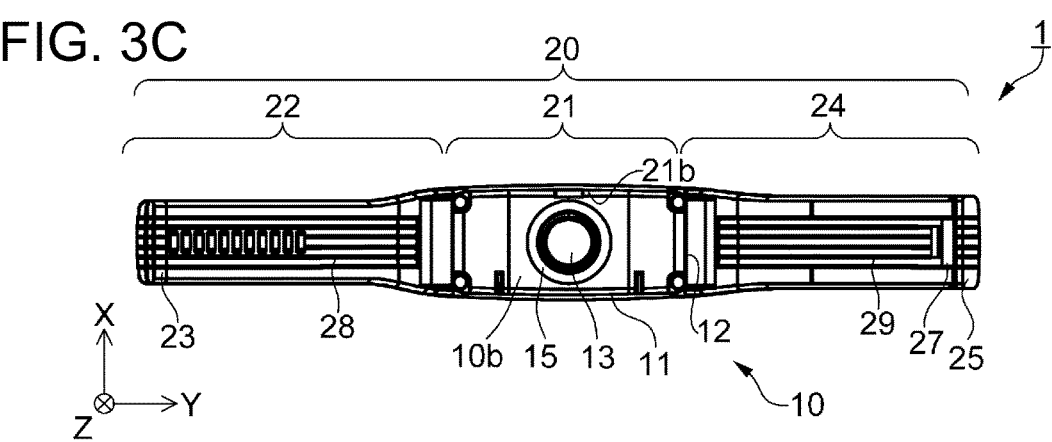

FIGS. 3A to 3C show the schematic configuration of the case unit and the buckle part. FIG. 3A is a front view of the measuring apparatus. FIG. 3B is a side view. FIG. 3C is a plan view (rear view), as viewed from the bottom side (detection unit). The configurations of the case unit 10 and the band 20 will be described in detail, referring to FIG. 3A to 6C.

In the front view shown in FIG. 3A, the top surface 10a of the case unit 10 (see FIG. 2) is covered with the main body part 21 of the band 20 and a pair of cover parts 16. Also, in the front view, the lateral part 11 of the case unit 10 is covered with the main body part 21 of the band 20. Therefore, the case unit 10 is not exposed in the front view.

Each of the cover parts 16 is substantially trapezoidal having an upper base and a lower base along the Y-axis direction, and the cover parts 16 are arranged in such a way that the lower bases thereof face each other, as viewed from the Z-axis direction (front direction). An opening extending along the Y-axis direction is provided between the pair of cover parts 16, and the light emitting unit 14 is exposed through the opening.

The width in the direction of extension (Y-axis direction) of the band 20 is the broadest in the main body part 21. The width of the main body part 21 is broader than the width of the case unit 10. The width of the first band part 22 becomes narrower as it moves away from the main body part 21, and then the width becomes a predetermined width W1. The width of the second band part 24 becomes narrower as it moves away from the main body part 21, and the width becomes a predetermined width W2.

In the side view shown in FIG. 3B, the part on the side of the top surface 10a, of the lateral part 11 of the case unit 10, is covered with the main body part 21 of the band 20, and the part on the side of the bottom surface 10b is exposed. A center part of the bottom surface 10b is a substantially flat surface. The end parts 12 situated at both ends of the lateral part 11 protrude in the −Z-axis direction (on the side installed on the wrist WR) from the bottom surface 10b. Therefore, the bottom surface 10b of the case unit 10 has curved parts 17 concavely curved toward the end parts 12 from the center part. The radius of curvature of the curved parts 17 is greater than the radius of curvature of the surface 21a of the main body part 21. Since the radius of curvature of the curved parts 17 on the inner side that contacts the wrist WR is greater than the radius of curvature of the surface 21a on the outer side, the thickness of the photoelectric pulse wave sensor unit 5 (see FIG. 2) can be absorbed by expanding the side of the surface 21a (top surface 10a of the case unit 10). Therefore, the tight contactability of the measuring apparatus 1 with the wrist WR will not be impaired. Also, the window part 13 as a detection unit protruding in the −Z-axis direction is provided in the center part of the bottom surface 10b.

In the plan view as viewed from the side of the bottom surface 10b, shown in FIG. 3C, the substantially rectangular case unit 10 is fitted in the opening 21b (see FIG. 2) provided in the middle of the band 20. The outer circumference of the case unit 10 is covered by the band 20 and the bottom surface 10b is exposed. The window part 13 provided in the center part of the bottom surface 10b is substantially circular in the plan view. Also, a ring-shaped bank part 15 surrounding the window part 13 is formed on the outside of the window part 13, as viewed in the plan view.

The bank part 15 is a rib formed integrally with the case unit 10 and provided in a convex shape protruding toward the wrist WR from the bottom surface 10b.

The window part 13 is a transparent convex lens-shaped member. In a preferred example, a transparent resin is used. The light emitted from the light emitting element of the photoelectric pulse wave sensor unit 5 (see FIG. 2) is transmitted through the window part 13 and cast on the wrist WR of the wearer. The light reflected by the blood vessels in the wrist WR is transmitted through the window part and received by the light receiving element of the photoelectric pulse wave sensor unit 5. Therefore, in order to detect biological information in a stable state with the photoelectric pulse wave sensor unit 5, it is desirable that, in the wearing state, the window part 13 should be stably held in tight contact with the wrist WR of the wearer.

The first band part 22 has a plurality of recessed groove parts 28 recessed from the surface, on the side (inner side or inner surface) facing the wrist WR. The second band part 24 has a plurality of groove parts 29 recessed from the surface, on the side facing the wrist WR. The plural groove parts 28, 29 extend respectively, for example, along the direction of extension of the band 20 (Y-axis direction) and are provided next to each other at substantially the same interval in the X-axis direction. The plural groove parts 28, 29 are provided to extend from the ends on the sides of the band parts 22, 24, of the main body part 21 including the case unit 10, and to open at the ends of the first band part 22 and the second band part 24 in the direction of extension of the band 20. Since the groove parts 28, 29 extend from the ends of the main body part 21 in this manner, the sweat and moisture generated in the main body part 21 including the case unit 10 can be released outside through the groove parts 28, 29.

Figure 4A:
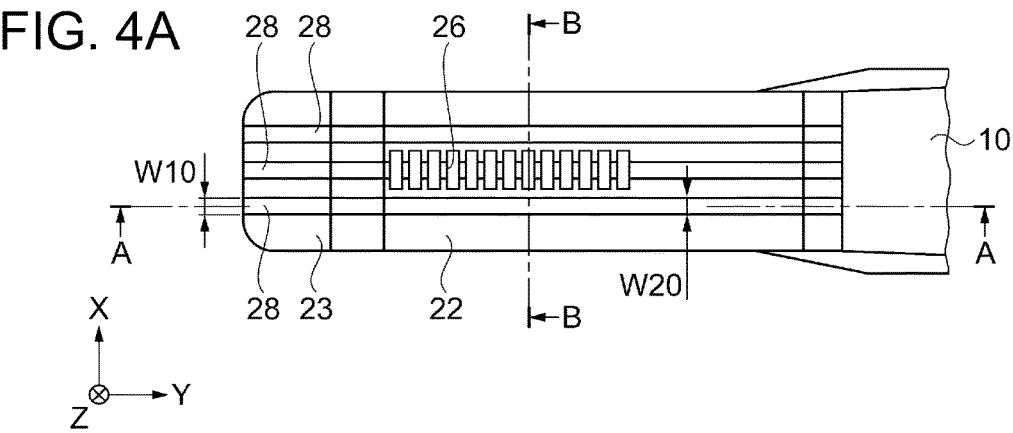
FIGS. 4A to 4C show details of the shape of the groove.
Figure 4B:
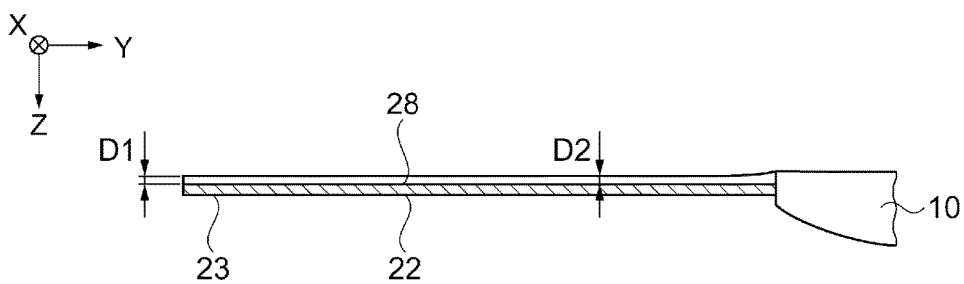
Figure 4C:
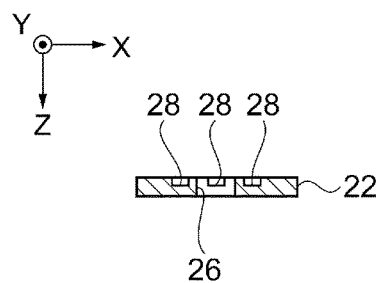

Details of the groove parts will be described, referring to FIGS. 4A to 4C. FIGS. 4A to 4C are enlarged views showing details of the groove parts. FIG. 4A is a plan view of a band, as viewed from the side facing the wrist WR. FIG. 4B is a cross-sectional view taken along A-A in FIG. 4A. FIG. 4C is a cross-sectional view taken along B-B in FIG. 4A. In the description below, the groove part 28 provided on the first band part 22 will be explained as an example. However, the groove parts 29 provided on the second band part 24 have a similar configuration.

FIGS. 4A to 4C show an example in which three groove parts 28 are provided on the first band part 22. Each of the three groove parts 28 is configured to be included in an imaginary space formed by a width W10 that is the dimension in the direction (X-axis direction) orthogonal to the direction of extension (Y-axis direction) and a depth D1 that is the dimension along the Z-axis direction. In other words, each of the three groove parts 28 with the width W10 and the depth D1 may be provided from the end of the main body part 21 including the case unit 10 to the end of the first band part 22. Also, a width W20 in the center part in the direction of extension in the first band part 22 may be formed to be narrower than the width W10 at the end of the first band part 22. Moreover, a depth D2 in the center part in the direction of extension in the first band part 22 may be formed to be shallower than the depth D1 at the end of the first band part 22.

In this configuration, each of the three groove parts 28 with the width W10 and the depth D1 is provided from the end of the main body part 21 including the case unit 10 to the end of the first band part 22. The groove part 28 in the center of the X-axis direction continues to the adjustment hole parts 26 as a plurality of hole parts provided in the first band part 22 so as to engage with a pawl part 35 (see FIGS. 6A to 6C) of the first plate 31 (see FIGS. 6A to 6C), described below. Since the groove part 28 and the adjustment hole parts 26 continue to each other, the sweat and moisture can also be released outside through the adjustment hole parts 26 continuing to the groove part 28, as well as through the groove parts 28. Therefore, the accumulation of the sweat and moisture on the wrist WR, which is the wearing part (living body) of the wearer, can be prevented and a more comfortable sensation of wearing can be achieved. As long as the groove part 28 is configured to continue to the adjustment hole parts 26 as hole parts, the sweat and moisture can be released outside through the adjustment hole parts 26. Therefore, the groove parts 28 may not be provided to open at the end of the first band part 22, and the ends of the groove parts 28 may be situated within the first band part 22.

Figure 5A:
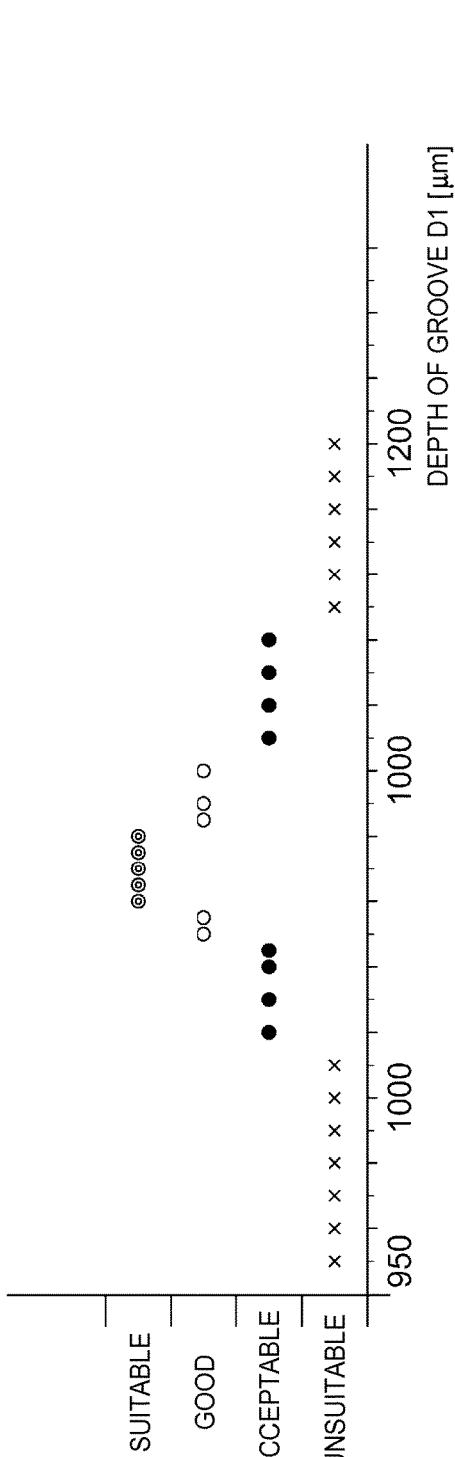
FIGS. 5A and 5B are graphs showing whether the depth of the groove and the width of the groove are proper or not.
Figure 5B:
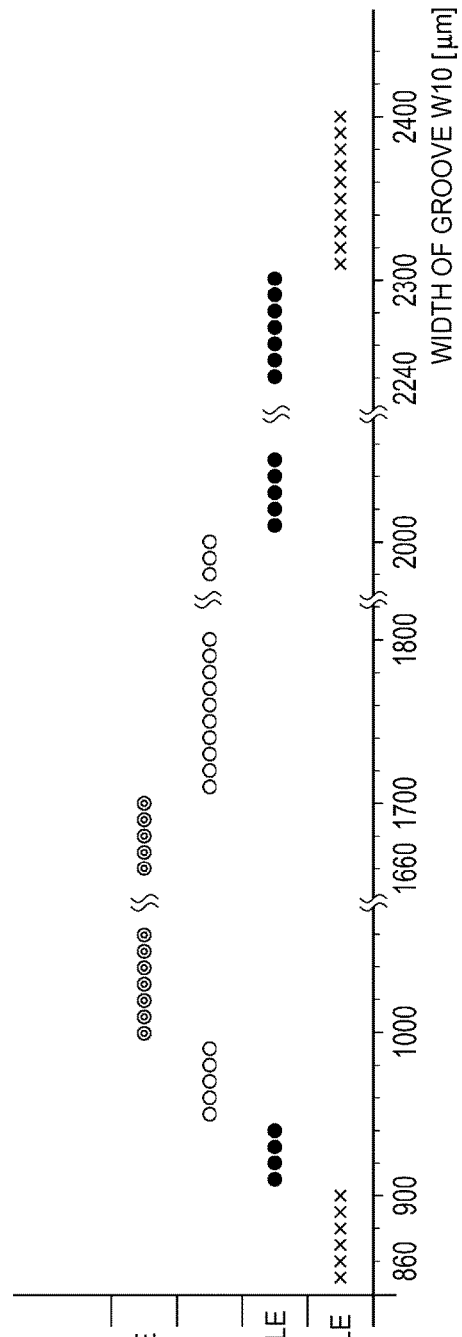

The inventors have found out that, if the depth D1 and the width W10 of the groove parts 28, 29 are set within a predetermined range, the sweat and moisture on the wrist WR, which is the wearing part (living body) of the wearer, can be released more effectively while the strength of the band 20 is secured. Hereinafter, preferable ranges of the depth D1 and the width W10 of the groove parts 28, 29 will be described, referring to FIGS. 5A and 5B. FIGS. 5A and 5B are graphs showing the results of verification about whether the depth D1 of the groove parts 28, 29 and the width W10 of the groove parts 28, 29 are proper or not. FIG. 5A shows the decision about each value of the depth D1 of the groove parts 28, 29. FIG. 5B shows the decision about each value of the width W10 of the groove parts 28, 29.

First, if the depth D1 of the groove parts 28, 29 is 1010 μm or less, the sweat and moisture cannot be discharged (released) sufficiently and therefore this depth is determined as unsuitable for use, as shown in FIG. 5A. In this case, it is presumed that, since the depth D1 of the groove parts 28, 29 is not sufficient, the skin of the wrist WR entering into the groove parts 28, 29 reduces the space in the groove parts 28, 29, making it difficult to discharge (release) the sweat and moisture. If the depth D1 is 1150 μm or more, the strength of the band 20 is considerably insufficient and there is a risk of cracking or damage if a load is applied. Therefore, this depth is determined as unsuitable.

Thus, the depth D1 of the groove parts 28, 29 can be set in a range excluding the range where it is determined as unsuitable for use, as described above. That is, it is preferable that the depth D1 of the groove parts 28, 29 is 1020 μm or more and 1140 μm or less. By providing the groove parts 28, 29 with such a depth D1, it is possible to sufficiently release outside the sweat exuded on the wrist WR of the arm AR of the wearer and the moisture that adheres at the time of washing the hands or the like, without lowering the strength (durability) of the band 20. In other words, inaccurate measurement (grasping) of the biological information (health state) such as the pulse waves of the wearer, due to a fall in the tight contactability between the window part 13 as a detection unit (sensor) and the living body (the skin of the wrist WR) caused by deformation of the band 20 or the like, can be prevented without spoiling the sensation of wearing experienced by the wearer.

It is more preferable that the depth D1 of the groove parts 28, 29 is 1050 μm or more and 1100 μm or less. By setting the depth D1 of the groove parts 28, 29 to 1050 μm or more and 1100 μm or less, it is possible to improve ventilation through the groove parts 28, 29 further and sufficiently release the sweat and moisture outside.

It is particularly preferable that the depth D1 of the groove parts 28, 29 is 1060 μm or more and 1080 μm or less. By setting the depth D1 of the groove parts 28, 29 to 1060 μm or more and 1080 μm or less, it is possible to sufficiently release the sweat and moisture outside and increase the flexibility of the band. Thus, the sensation of fitting (sensation of wearing) on the wearing part (living body) can be improved.

Next, if the width W10 of the groove parts 28, 29 is 900 μm or less, the sweat and moisture cannot be discharged (released) sufficiently and therefore this width is determined as unsuitable for use, as shown in FIG. 5B In this case, it is presumed that, since the width W10 of the groove parts 28, 29 is not sufficient, the skin of the wrist WR entering into the groove parts 28, 29 reduces the cross-sectional area in the groove parts 28, 29, making it difficult to discharge (release) the sweat and moisture. If the width W10 is 2310 μm or more, the strength of the band 20 is considerably insufficient and there is a risk of cracking or damage if a load is applied. Moreover, the thickness of the bank-like wall part forming the groove parts 28, 29 is reduced and the pressure to bring the window part 13 as a detection unit into tight contact concentrates on the wall part, thus increasing the biting into the wrist WR and impairing the sensation of wearing. Therefore, this width is determined as unsuitable.

Thus, the width W10 of the groove parts 28, 29 can be set in a range excluding the range where it is determined as unsuitable for use, as described above. That is, it is preferable that the width W10 of the groove parts 28, 29 is 910 µm or more and 2300 µm or less. By providing the groove parts 28, 29 with such a width W10, it is possible to sufficiently release outside the sweat exuded on the wrist WR of the arm AR of the wearer and the moisture that adheres at the time of washing the hands or the like, without lowering the strength (durability) of the band 20. In other words, inaccurate measurement (grasping) of the biological information (health state) such as the pulse waves of the wearer, due to a fall in the tight contactability between the window part 13 as a detection unit (sensor) and the living body (the skin of the wrist WR) caused by deformation of the band 20 or the like, can be prevented without spoiling the sensation of wearing experienced by the wearer.

It is more preferable that the width W10 of the groove parts 28, 29 is 950 µm or more and 2000 µm or less. By setting the width W10 of the groove parts 28, 29 to 950 µm or more and 2000 µm or less, it is possible to improve ventilation through the groove parts 28, 29 further and sufficiently release the sweat and moisture outside.

It is particularly preferable that the width W10 of the groove parts 28, 29 is 1000 µm or more and 1700 µm or less. By setting the width W10 of the groove parts 28, 29 to 1000 µm or more and 1700 µm or less, it is possible to sufficiently release the sweat and moisture outside and increase the flexibility of the band. Moreover, the width of the bank-like wall part formed by the groove parts 28, 29 (contact part with the wearing part (living body) of the wearer) increases, enabling a reduction in the biting of the wall part into the wearing part (living body) of the wearer. Thus, the sensation of fitting (sensation of wearing) experienced by the wearer can be improved.

The band 20 includes the first band part 22 and the second band part 24. By providing the groove parts 28, 29 on the first band part 22 and the second band part 24, it is possible to release the sweat and moisture from the entire band 20. Also, the window part 13 as a detection unit (sensor) can be easily brought in tight contact with the wearing part (wrist WR) without spoiling the sensation of wearing.

Also, since the first band part 22 and the second band part 24 have the pluralities of groove parts 28, 29, the substantial area of the first band part 22 and the second band part 24 in contact with the wrist WR of the wearer in the wearing state can be reduced.

Moreover, since the pluralities of groove parts 28, 29 are provided along the direction of extension of the band 20 (Y-axis direction), a shift in the direction of the width (X-axis direction intersecting with the Y-axis direction) of the measuring apparatus 1 in the wearing state can be restrained.

Configuration of Buckle Part

Figure 6A:
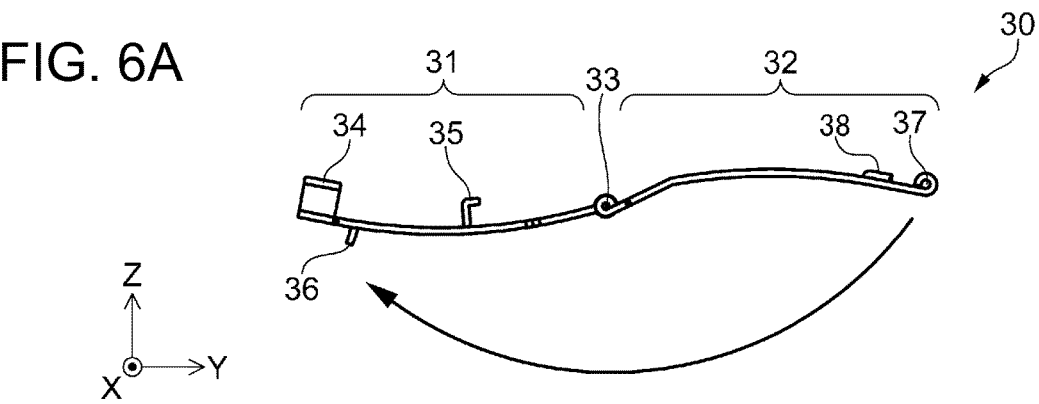
FIGS. 6A to 6C schematically show the configuration of a buckle part and the connection configuration with the band.
Figure 6B:
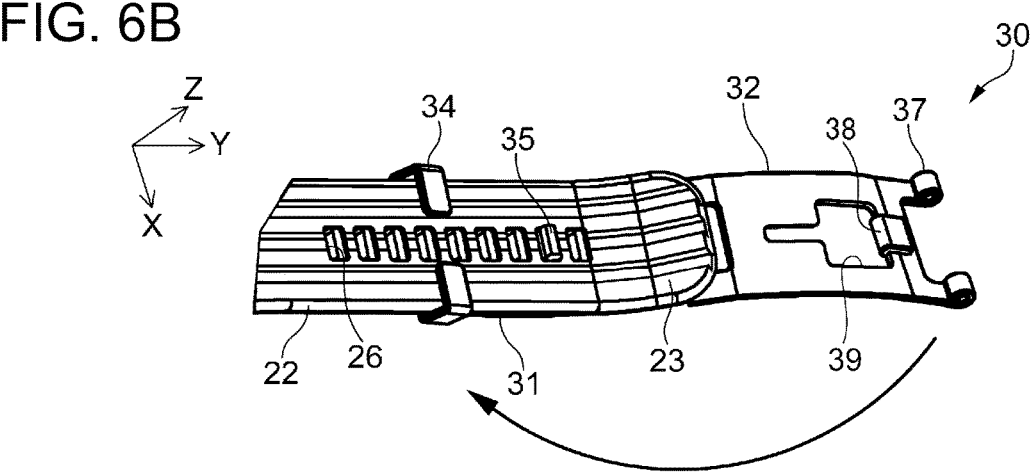
Figure 6C:
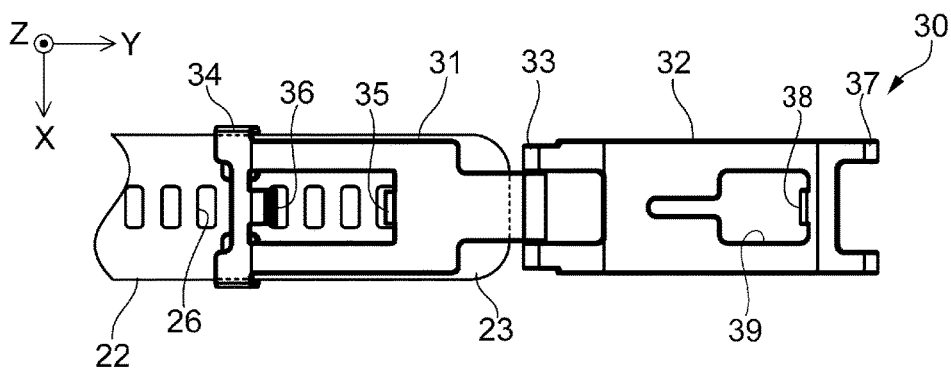
Figure 7A:
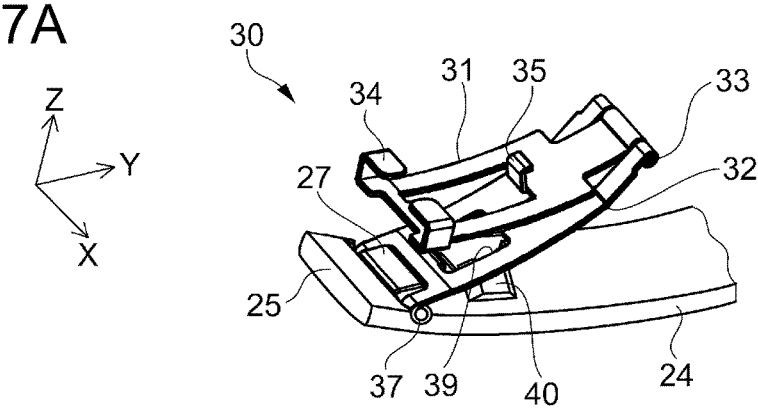
FIGS. 7A to 7C schematically show the configuration of the buckle part and the connection configuration with the band.
Figure 7B:
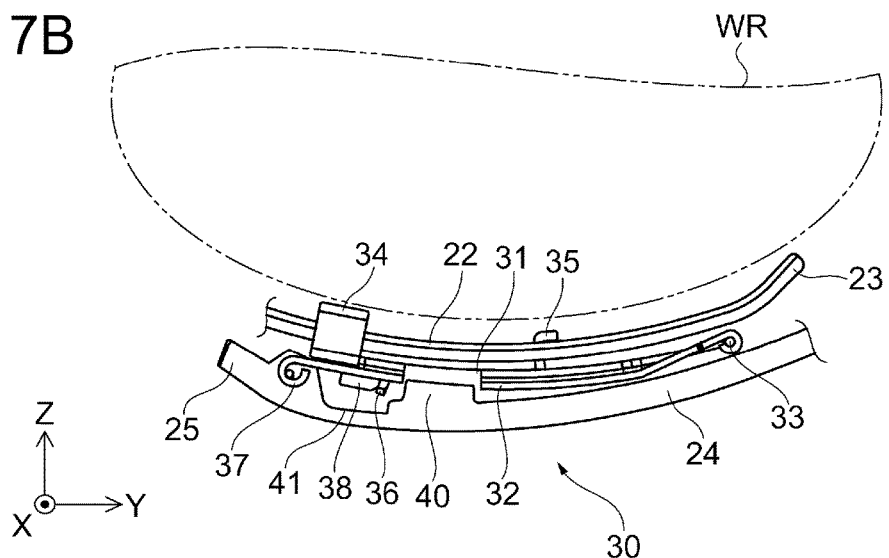
Figure 7C:
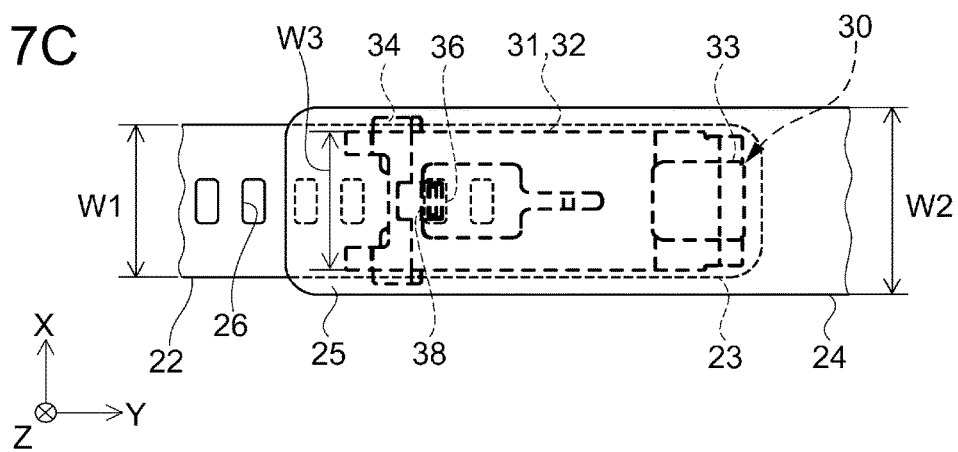

The configuration of the buckle part of the measuring apparatus 1 and the connection structure with the band will be described, referring to FIGS. 6A to 6C and FIGS. 7A to 7C. FIGS. 6A to 6C and FIGS. 7A to 7C show the configuration of the buckle part and the connection structure with the band. More specifically, FIG. 6A is a side view of the buckle part in the open state. FIG. 6B is a perspective view of the buckle part, as viewed from the inner side, in the state where the first band part is connected to the first plate. FIG. 6C is a plan view showing the state of FIG. 6B, as viewed from the outer side. FIG. 7A is a perspective view of the buckle part, as viewed from the inner side, in the state where the second band part is connected to the second plate. FIG. 7B is a side view of the band and the buckle part in the wearing state. FIG. 7C is a plan view showing the state of FIG. 7B, as viewed from the outer side. In FIG. 7B, a cross-section of the wrist WR of the wearer is schematically shown by dashed double-dotted lines.

Figure 9:
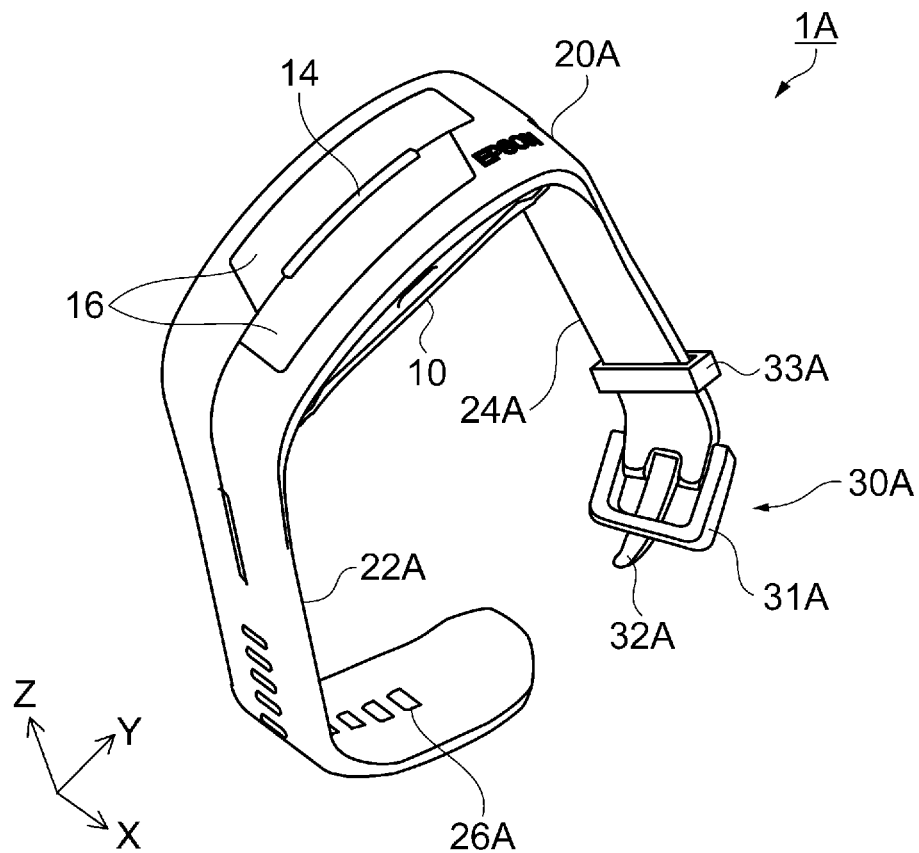
FIG. 9 is a perspective view showing another configuration of the buckle part.

Also, with respect to a measuring apparatus 1A having a buckle part with another configuration, the configuration of the buckle part and the connection structure with the band will be described, referring to FIG. 9. FIG. 9 is a perspective view showing the configuration of the buckle part with another configuration, of the measuring apparatus 1A, and the connection structure with the band.

First, referring to FIGS. 6A to 6C and FIGS. 7A to 7C, the configuration of the buckle part 30 and the connection structure with the band 20 will be described. As shown in FIG. 6A, in the buckle part 30, one end of the first plate 31 and one end of the second plate 32 are axially supported by the hinge part 33 so as to be able to swivel toward and away from each other. The first plate 31 has a guide part 34 provided at the other end, a pawl part 35 extending to the inner side, and a pawl part 36 extending to the outer side. The second plate 32 has a connection part 37 provided at the other end and a protruding part 38 protruding to the inner side in the open state.

In the buckle part 30, the side of the connection part 37 of the second plate 32 is made to swivel in the direction of the arrow, about the hinge part 33 as the swivel axis, and the second plate 32 is thus folded to be on top of the outside of the first plate 31, as shown in FIG. 6B, thus establishing the wearing state. In the wearing state, the pawl part 36 of the first plate 31 and the protruding part 38 of the second plate 32 engage with each other, thus holding the wearing state where the buckle part 30 is folded. A positioning hole 39 is formed next to the protruding part 38. The positioning hole 39 is a substantially rectangular hole along the direction of extension of the second plate 32.

In the wearing state shown in FIG. 7B, the first band part 22 is arranged at the closest position to the wrist WR (inner side), and the first plate 31, the second plate 32, and the second band part 24 are arranged in this order toward the opposite side of the wrist WR (outer side). From this wearing state, the pawl part 36 of the first plate 31 and the protruding part 38 of the second plate 32 are disengaged from each other and the side of the connection part 37 of the second plate 32 is unfolded away from the first plate 31 toward the outer side. Thus, the open state shown in FIG. 6A is established.

As shown in FIGS. 6B and 6C, the first band part 22 is connected to the first plate 31 by allowing one of the plurality of adjustment hole parts 26 to be engaged with the pawl part 35 of the first plate 31. By properly selecting the adjustment hole part 26 to engage with the pawl part 35, it is possible to adjust the effective length of the band 20 in the wearing state and thus adjust the tightening force of the band 20. Similarly, in the open state, one of the adjustment hole parts 26 and the pawl part 35 engage with each other, holding the state where the first band part 22 and the first plate 31 are connected together. Therefore, once the tightening force of the band 20 is adjusted, the adjusted tightening force is reproduced even if the installation on and removal from the wrist WR are repeated.

As shown in FIG. 6B, the distal end part 23 of the first band part 22 is bent to the inner side, that is, to the side opposite to the first plate 31. Therefore, when the first plate 31 and the second plate 32 are folded on top of each other from the open state so as to establish the wearing state, the distal end part 23 can be prevented from warping toward the first plate 31 (outer side) and getting caught between the first band part 22 and the first plate 31 or between the second band part 24 and the second plate 32 (FIG. 7B).

As shown in FIG. 7A, the second band part 24 is connected to the second plate 32 by having the connection part 37 of the second plate 32 and the connection part 27 axially supported by a pin or the like so as to be able to swivel. The distal end part 25 of the second band part 24 is bent to the inner side, that is, toward the wrist WR. On the second band part 24, a protruding part 40 is formed at a position that coincides with the positioning hole 39 in the second plate 32 when the buckle part is folded. As the buckle part 30 is folded and the second plate 32 and the second band part 24 are placed on top of each other, the protruding part 40 is fitted in the positioning hole 39. Thus, misalignment of the two in the direction of the width of the second band part 24 can be restrained. As described above, in the wearing state shown in FIG. 7B, the second band part 24 is arranged on the outermost side. Since the distal end part 25 of the second band part 24 is bent to the inner side, the distal end part 25 can be restrained from getting caught on the sleeves of the clothes or the like in the wearing state.

Also, in the second band part 24, a recess 41 is formed at a position that coincides with the pawl part 36 when the measuring apparatus is worn, as shown in FIG. 7B. The recess 41 is formed in the shape of a hollow (not shown) in the middle in the direction of the width of the second band part 24 and avoids the protrusion of the pawl part 36 and the protruding part 38. Thus, the second band part 24 is restrained from floating up.

As shown in FIG. 7C, the width W1 of the first band part 22 and the width W2 of the second band part 24 are in the relation of W1<W2. That is, the width W2 of the second band part 24 arranged to the outer side in the wearing state is broader (greater) than the width W1 of the first band part 22 arranged to the inner side. Also, if the width of the part having the greatest width of the buckle part 30 (in this embodiment, the guide part 34) is W3, it is preferable that W3<W2 holds. That is, it is preferable that the width W2 of the second band part 24 is broader (greater) than the width W3 of the buckle part 30 arranged more to the inner side than the second band part 24 in the wearing state.

If the width W2 of the second band part 24 arranged on the outermost side is broader than the width W1 of the first band part 22 and the width W3 of the buckle part 30, the first band part 22 and the buckle part 30 are covered by the second band part 24. Thus, in the wearing state, the buckle part 30 made of a metal material is restrained from getting caught on the sleeves of the clothes or from contacting an obstacle or the like, and the appearance is improved as well.

Here, it is preferable that at least the parts of the first band part 22 and the second band part 24 that contact each other are grained, that is, processed to create ruggedness. If the parts contacting each other are grained, the frictional force generated when the first band part 22 and the second band part 24 rub each other is reduced, making the rubbing smoother. Therefore, compared with the case where the graining is not carried out, the distal end part 23 of the first band part 22 and the distal end part 25 of the second band part 24 are restrained from getting caught at the time of installation. The installation and removal of the measuring apparatus 1 can be carried out easily.

It is also preferable that the parts of the first band part 22 and the second band part 24 that contact the wrist WR are grained. If the parts contacting the wrist WR are grained, the effective contact area per unit area of the first band part 22 and the second band part 24 can be reduced, compared with the case where the graining is not carried out. Thus, in the wearing state, the discomfort experienced by the wearer due to the tight contact between the first band part 22 and the second band part 24, and the wrist WR, can be restrained.

Next, the wearing state of a measuring apparatus 1A having a buckle part with another configuration will be described, referring to FIG. 9. As shown in FIG. 9, the measuring apparatus 1A has a case unit 10 as an apparatus main body, a band 20A which fixes the case unit 10 to the wrist WR (see FIG. 10), and a buckle part 30A which connects to the band 20A.

The band 20A covers the front side of the case unit 10 along the Y-axis direction and extends from both sides of the case unit 10. The band 20A includes a first band part 22A extending toward one end from the part where the case unit 10 is arranged, and a second band part 24A extending toward the other end. The band 20A in a single-piece (initial) state is in an inverted U-shape in which the first band part 22A and the second band part 24A hang down to the left and right from the part in the middle of the band 20A where the case unit 10 is arranged, as the top, as viewed in a side view. The buckle part 30A and a free loop 33A are provided at the end of the second band part 24A.

The buckle part 30A includes a frame 31A and a buckle tongue 32A provided in such a way as to be rotatable about an axial pin (not shown in FIG. 9) provided at the end of the second band part 24A. The buckle part 30A can be connected to the first band part 22A by having the buckle tongue 32A inserted in an installation hole 26A formed in the first band part 22A, within the frame 31A. That is, the first band part 22A and the second band part 24A can be connected together. In this way, the buckle part 30A is a component having the function of adjusting the overall length of the band 20A. The free loop 33A is a ring-shaped component which is installed movably on the second band part 24A more to the side of the case unit 10 than the buckle part 30A and has the function of holding the end (tip) of the first band part 22A.

Installation of Measuring Apparatus

Figure 8:
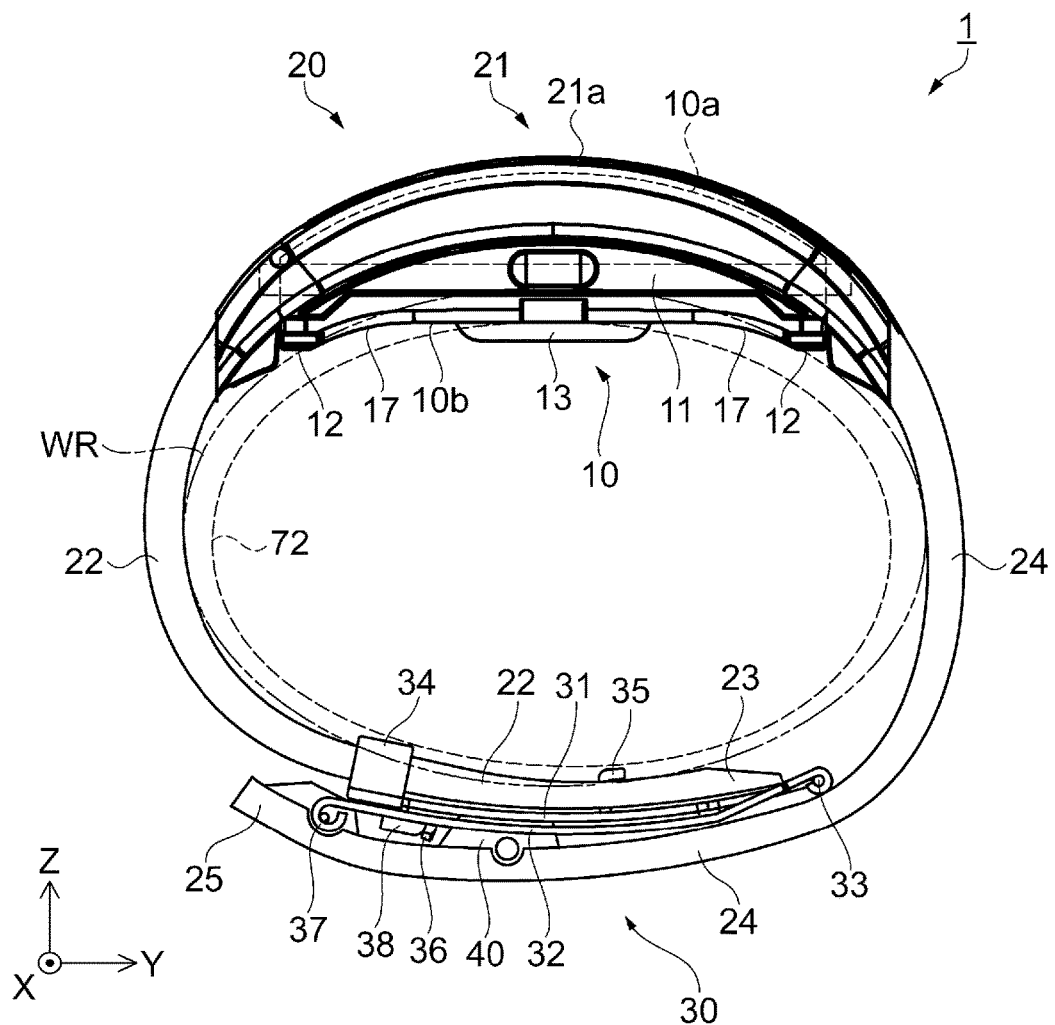
FIG. 8 is a side view showing a wearing state.
Figure 10:
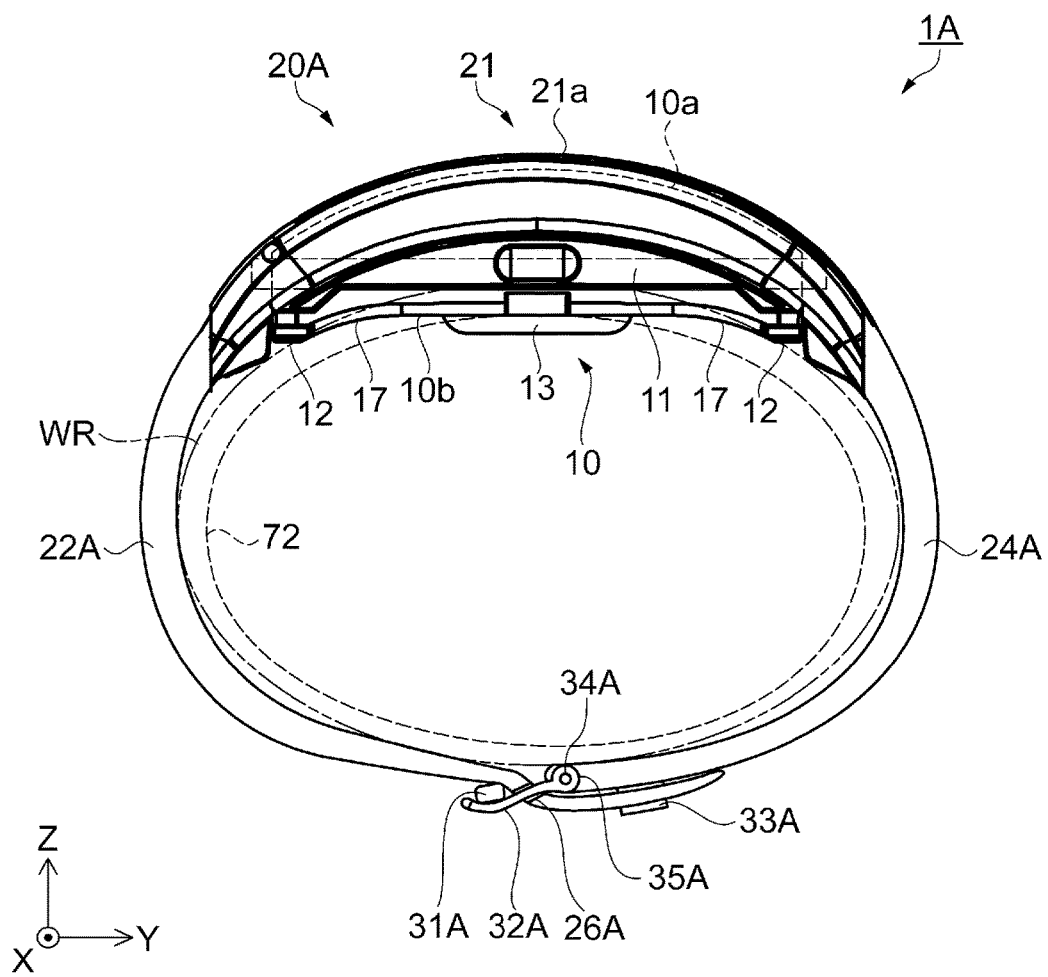
FIG. 10 is a side view showing a wearing state with another configuration of the buckle part.

Next, the wearing state of the measuring apparatus 1 will be described, referring to FIG. 8. FIG. 8 is a side view showing the wearing state of the measuring apparatus. Also, the wearing state of the measuring apparatus 1A having a buckle part with another configuration will be described, referring to FIG. 10. FIG. 10 is a side view showing the wearing state of the measuring apparatus 1A having a buckle part with another configuration.

First, the wearing state of the measuring apparatus 1 will be described. As shown in FIG. 8, the measuring apparatus 1 is installed on the wrist WR by having the buckle part 30 folded. The measuring apparatus 1 is installed, tightened with a necessary force to bring the window part 13 as a detection unit (sensor) into tight contact with the wrist WR with proper strength. That is, to secure tight contactability between the window part 13 as a detection unit (sensor) and the wrist WR, the length of an inner circumference 72 is set to be slightly shorter than the circumferential length of the wrist WR. Then, with a position setting between the buckle part 30 and an adjustment hole, and a proper pressurizing force by the elasticity of the band 20, the window part 13 as a detection unit (sensor) can be brought into tight contact with the wrist WR with proper strength.

In this manner, at the time of installing the measuring apparatus 1, the buckle part 30 is extended to its length, then the pursed hand is inserted in the large ring-shaped opening formed in this state, and subsequently the buckle part 30 is folded to be shorter at the wearing position on the wrist WR. Thus, the measuring apparatus 1 can be easily installed. Therefore, according to the measuring apparatus 1, tight contactability (wearability) necessary for stable measurement of biological information can be secured. Also, the measuring apparatus 1 capable of stably measuring biological information even if installation and removal are repeated can be provided.

Next, the wearing state of the measuring apparatus 1A having a buckle part with another configuration will be described, referring to FIG. 10. As shown in FIG. 10, the measuring apparatus 1A is installed on the wrist WR by having the first band part 22A and the second band part 24A connected together with the buckle part 30A. Specifically, in the case of installing the measuring apparatus 1A on the wrist WR with the band 20A, the end (tip) of the first band part 22A is inserted in the frame 31A provided on the second band part 24A in such a way as to be able to swivel via an axial pin 34A, and the buckle tongue 32A via a bearing part 35A installed in such a way as to be able to swivel about the axial pin 34A is inserted into the installation hole 26A, at a position that establishes the state where the predetermined contactability is secured.

In this manner, the measuring apparatus 1A is installed, tightened with a necessary force to bring the window part 13 (not shown) as a detection unit (sensor) into tight contact with the wrist WR with proper strength. That is, with a position setting between the buckle tongue 32A and the installation hole 26A, and a proper pressurizing force based on the elasticity of the band 20A, the window part 13 as a detection unit (sensor) can be brought into tight contact with the wrist WR with proper strength.

According to the biological information measuring apparatus 1 (measuring apparatus 1 or measuring apparatus 1A) according to Embodiment 1 described above, since the groove parts 28, 29 are provided on the first band part 22 and the second band part 24 forming the band 20, the sweat and moisture can be released from the band 20 and the wrist WR or the like. Also, since the groove parts 28, 29 are provided, the contact area between the band 20 and the wearing part (skin) can be reduced and therefore perspiration can be restrained. Thus, it is more difficult for the sweat and moisture to flow out to the back side of the case unit 10, where the window part 13 as a detection unit (sensor) is provided, and a fall in measuring accuracy due to the attachment of the sweat and moisture to the window part 13 can be restrained. Also, the discomfort due to the accumulation of the sweat and moisture can be prevented and the window part 13 as a detection unit (sensor) can be easily brought in tight contact with the wearing part (wrist WR) without spoiling the sensation of wearing.

Modifications of Groove Parts

Figure 12A:
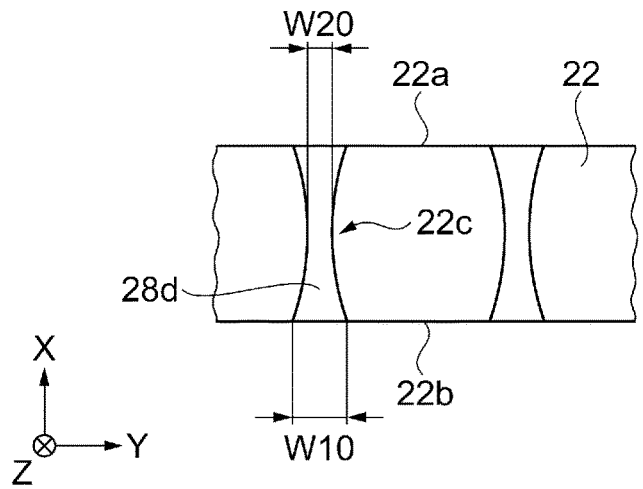
FIGS. 12A and 12B show a modification of the groove part.
Figure 12B:
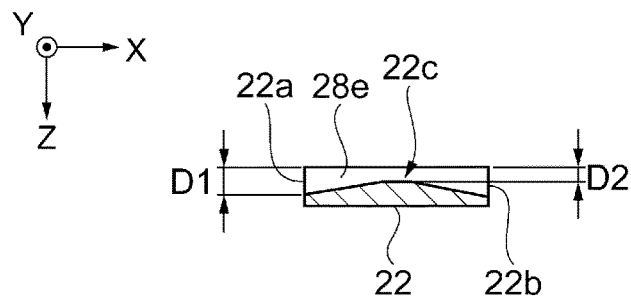
Figure 13:
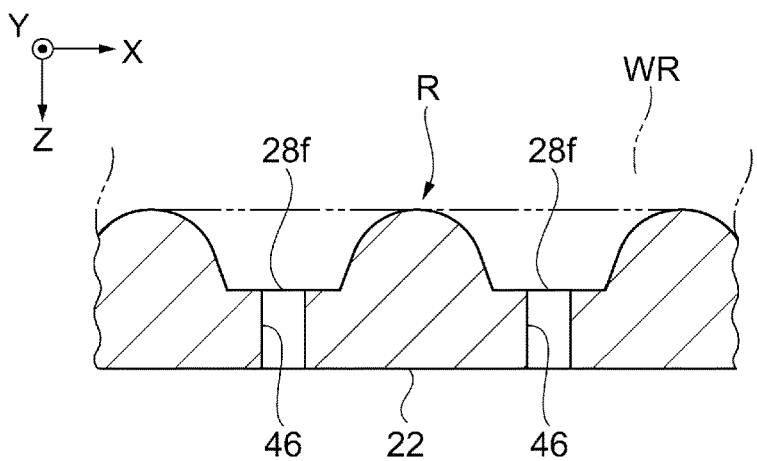
FIG. 13 is a cross-sectional view showing a modification of the groove part.

The above embodiment is described, using an example in which, on each of the first band part 22 and the second band part 24, the three groove parts 28, 29 extend along the direction of extension of the band 20 (Y-axis direction) and are arranged next to each other at substantially the same interval in the X-axis direction. However, the configuration of the groove parts 28, 29 is not limited to this example. For example, the configurations in the following modifications achieve effects similar to the above. The modifications will be described in order below, referring FIGS. 11A to 11E, FIGS. 12A and 12B, and FIG. 13. FIGS. 11A to 11E are plan views showing modifications of the groove parts. FIGS. 12A and 12B show another modification of the groove parts. FIG. 12A is a plan view. FIG. 12B is a side cross-sectional view of a groove part. FIG. 13 is a cross-sectional view showing a modification of the groove parts. In the description below, the groove parts 28 are taken as a representative example. However, similar configurations can apply to the groove parts 29 as well.

Modification 1

Figure 11A:
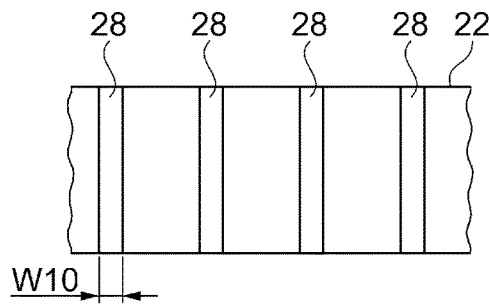
FIGS. 11A to 11E are plan views showing modifications of the groove.

In Modification 1 shown in FIG. 11A, a plurality of groove parts 28 is provided on the first band part 22, along a direction (X-axis direction) intersecting with the direction of extension of the band 20 (Y-axis direction) and arranged next to each other at substantially the same interval in the Y-axis direction. Here, the width W10 and the depth D1 (not shown) of the groove parts 28 are configured to be similar to those in the first embodiment. The interval between the groove parts 28 may not necessarily be substantially the same. For example, the interval may be narrowed sequentially as it goes from the side of the case unit 10 (see FIGS. 1A and 1B) toward the distal end, or the interval may be narrowed and the number of groove parts 28 may be increased at the site in tight contact with the wrist WR so as to improve ventilation.

With such groove parts 28 according to Modification 1 provided, for example, when the measuring apparatus is installed on a curved surface such as the wrist WR (see FIG. 1A) of the arm AR, the band can be easily deformed and the sensation of wearing (sensation of fitting) can be improved.

Modification 2

Figure 11B:
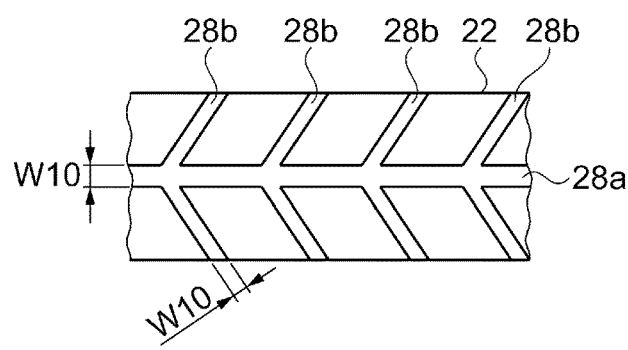

In Modification 2 shown in FIG. 11B, a first groove part 28a extending along the direction of extension of the band 20 (Y-axis direction) is provided at a center part in the direction of the width of the first band part 22 (X-axis direction), and a plurality of second groove parts 28b extending along two directions intersecting the first groove part 28a (in this example, XY-direction and −XY-direction) and arranged next to each other in the Y-axis direction are provided. The first groove part 28a and the second groove parts 28b are connected together and thus configured in a so-called lattice form (mesh form). Here, the width W10 and the depth D1 (not shown) of the first groove part 28a and the second groove parts 28b are configured to be similar to those in the first embodiment. Also, a plurality of first groove parts 28a may be provided. The number of the second groove parts 28b may be one or more. Moreover, the second groove parts 28b in a single direction (for example, from the XY-direction to the −XY-direction) may intersect with the first groove part 28a.

Modification 3

Figure 11C:
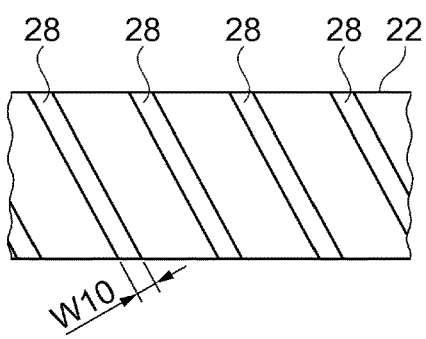

In Modification 3 shown in FIG. 11C, a plurality of groove parts 28 obliquely crossing the direction of the width of the first band part 22 (X-axis direction) is provided on the first band part 22, next to each other at substantially the same interval. Here, the width W10 and the depth D1 (not shown) of the groove parts 28 are configured to be similar to those in the first embodiment. As in Modification 1, the interval between the groove parts 28 may not necessarily be substantially the same. The direction of inclination (gradient) is not particularly specified.

Modification 4

Figure 11D:
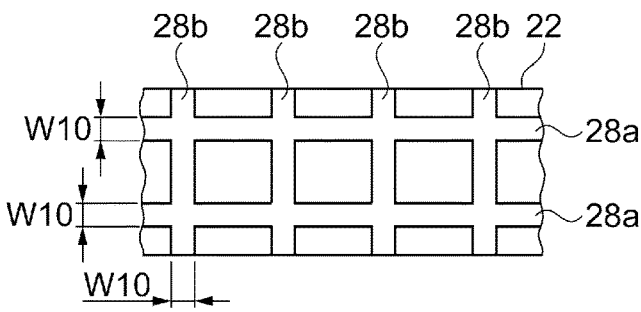

In Modification 4 shown in FIG. 11D, two first groove parts 28a extending along the direction of extension of the first band part 22 (Y-axis direction) and a plurality of second groove parts 28b extending along a direction (in this example, the X-axis direction) intersecting with the first groove parts 28a and arranged next to each other in the Y-axis direction are provided on the first band part 22. The first groove parts 28a and the second groove parts 28b are connected to each other. Here, the width W10 and the depth D1 (not shown) of the first groove parts 28a and the second groove parts 28b are configured to be similar to those in the first embodiment. Also, the number of the first groove parts 28a may be one or more, and the number of the second groove parts 28b may be one. The second groove parts 28b may be provided at substantially the same interval or at different intervals.
Modification 5

Figure 11E:
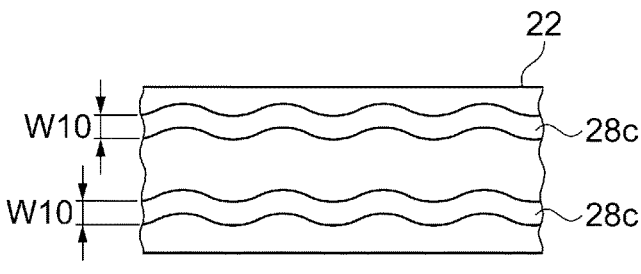

In Modification 5 shown in FIG. 11E, two groove parts 28c extending in the shape of curved lines (wavy lines) along the direction of extension of the first band part 22 (Y-axis direction) are provided on the first band part 22. Here, the width W10 and the depth D1 (not shown) of the groove parts 28c are configured to be similar to those in the first embodiment. Although not shown, second groove parts extending in a direction intersecting with the groove parts 28c may be combined with the groove parts 28c (a configuration similar to Modification 4).
Modification 6

In Modification 6 shown in FIGS. 12A and 12B, groove parts 28d are provided in the arrangement described in Modification 1. As shown in FIG. 12A, the groove parts 28d increase in width dimension as it goes toward end parts 22a, 22b on both sides from a center part 22c in the direction of the width of the first band part 22 (X-axis direction). That is, in the groove parts 28d, the width W20 of the part in the center part 22c is the smallest. The width dimension increases sequentially as it goes toward the end parts 22a, 22b on both sides, and the width W10 of the part opening at the end parts 22a, 22b on both sides is the largest. In this example, the sidewalls on both sides of each groove part 28d are arcuate, as viewed in a plan view. However, the sidewalls may be in the form of straight lines or a mixture of straight lines and curved lines.

As shown in FIG. 12B, the groove parts 28d also increase in depth dimension in the direction of the thickness of the first band part 22 (Z-axis direction) as it goes toward the end parts 22a, 22b on both sides from the center part 22c in the direction of the width of the first band part 22 (X-axis direction). That is, in the groove parts 28d, the depth D2 of the part in the center part 22c is the shallowest. The depth dimension increases sequentially as it goes toward the end parts 22a, 22b on both sides, and the depth D1 of the part opening at the end parts 22a, 22b on both sides is the deepest. In this example, the bottom part of each groove part 28d is in the form of a straight line. However, the bottom part may be in the form of a straight line or a mixture of straight lines and curved lines.

Each groove part 28d is configured to be included in an imaginary space formed by the width W10 and the depth D1, as described in the first embodiment. In other words, each groove part 28d is formed in such a way that the width W10 and the depth D1 are maximum dimensions. With such groove parts 28d, a large opening area of the end parts 22a, 22b of the band is provided. Therefore, ventilation can be improved further, making it easier to release the sweat and moisture outside.
Modification 7

In Modification 7 shown in FIG. 13, groove parts 28f are provided, thereby forming arcuate top parts R of bank-like wall parts. Also, hole parts 46 penetrating the first band part 22 from the bottom parts of the groove parts 28f are formed.

According to such a configuration, the arcuate top parts R contact the wrist WR, thus improving the sensation of wearing. Also, since the sweat and moisture can be released outside from the groove parts 28f and the hole parts 46 continuing to the groove parts 28f, the accumulation of the sweat and moisture on the wearing part (living body) can be prevented and a more comfortable sensation of wearing can be achieved.

If the groove parts 28f are configured to continue to the hole parts 46, the sweat and moisture can be released outside through the hole parts 46. Therefore, the groove parts 28f may not be provided to the ends of the first band part 22, and the ends of the groove parts 28f may be provided inside the first band part 22.

Embodiment 2

Next, Embodiment 2 of the invention will be described, referring to the drawings.

A biological information measuring apparatus according to Embodiment 2 (hereinafter referred to as a measuring apparatus) is a heart rate monitoring apparatus which is installed on a living body (for example, a human body) whose biological information is to be measured, and which measures biological information such as pulse waves and pulse rate (heart rate), as in the embodiment described above. In the drawings described below, the dimension and proportion of each component may be different from those of the actual component according to need, in order to show each components with a size such that the component can be recognized in the drawings.

First, before explaining a heart rate monitoring apparatus 1020 as the biological information measuring apparatus according to Embodiment 2, a related-art example of the heart rate monitoring apparatus as the biological information measuring apparatus according to Embodiment 2 will be explained, referring to FIG. 14.

Figure 14:
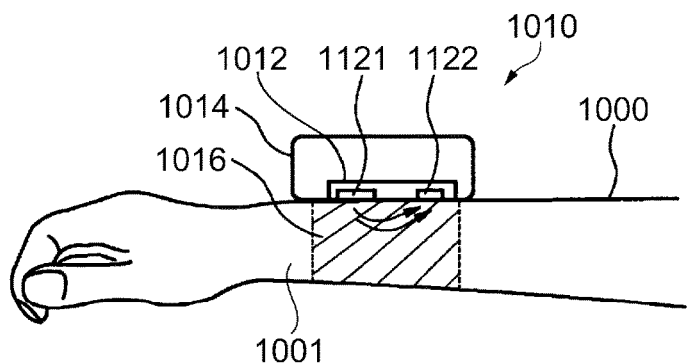
FIG. 14 is a cross-sectional view showing a traditional example of a biological information measuring apparatus according to Embodiment 2.

FIG. 14 is a cross-sectional view showing a heart rate monitoring apparatus 1010 as a biological information measuring apparatus in a related-art example which measures a physiological parameter (biological information) of a user (subject) 1000 (in FIG. 14, the user's arm is shown) wearing the heart rate monitoring apparatus. The heart rate monitoring apparatus 1010 includes a sensor 1012 which measures heart rate as at least one physiological parameter of the user 1000, and a case 1014 housing the sensor 1012. The heart rate monitoring apparatus 1010 is installed on an arm 1001 of the user 1000 with a fixture part 1016 (for example, a band).

The sensor 1012 is a heart rate monitoring sensor having a light emitting element 1121 and a light receiving element 1122, which are as two sensor elements, and configured to measure or monitor heart rate. However, the sensor 1012 may be a sensor which measures one or more physiological parameters (for example, heart rate, blood pressure, expiratory volume, skin conductivity, skin humidity, and the like). If the case 1014 has a band-type housing, the apparatus can be used as a wristwatch-type monitoring apparatus which is used, for example, in sports. The shape of the case 1014 may be any shape that can hold the sensor 1012 at a desired position mainly in relation to the user 1000. The case 1014 may be able to house additional elements arbitrarily, such as a battery, processing unit, display, or user interface.

The biological information measuring apparatus in the related-art example is the heart rate monitoring apparatus 1010 for monitoring the heart rate of the user. The sensor 1012 is an optical sensor made up of the light emitting element 1121 and the light receiving element 1122. The optical heart rate monitor using the optical sensor depends on the light emitting element 1121 (usually, an LED is used) as a light source which casts light on the skin. Apart of the light cast on the skin from the light emitting element 1121 is absorbed by the blood flowing through the blood vessels under the skin, but the remaining part of the light is reflected and exits the skin. The reflected light is captured by the light receiving element 1122 (usually, a photodiode is used). The light receiving signal from the light receiving element 1122 is a signal including information corresponding to the amount of blood flowing through the blood vessels. The amount of blood flowing through the blood vessels changes according to the pulsation of the heart. Thus, the signal on the light receiving element 1122 changes according to the pulsation of the heart. That is, the change in the signal of the light receiving element 1122 corresponds to the pulses of the pulse rate. The number of pulses per unit time (for example, per 10 seconds) is counted, thus obtaining the number of times of the heart beating during a minute (that is, heart rate).

Figure 15:
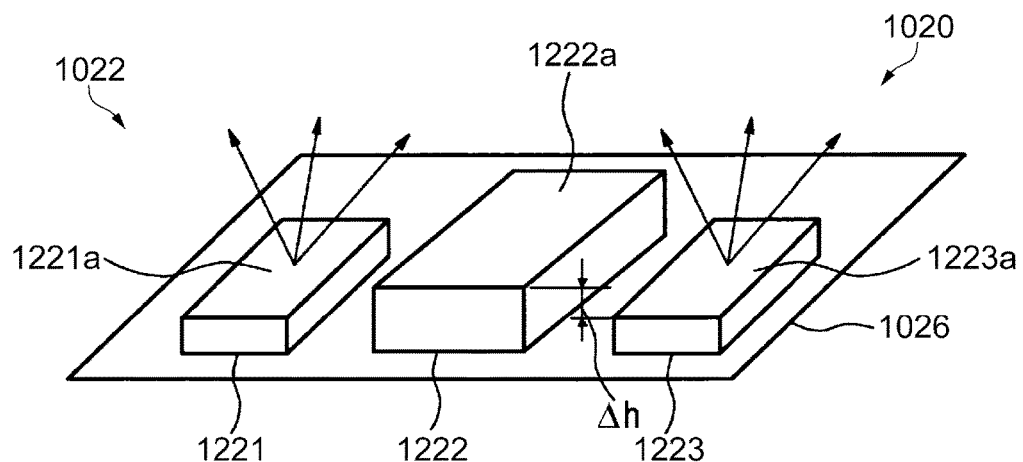
FIG. 15 is a perspective view showing the biological information measuring apparatus according to Embodiment 2.

Hereinafter, the heart rate monitoring apparatus 1020 as the biological information measuring apparatus according to Embodiment 2 will be described, referring to FIG. 15. FIG. 15 is a perspective view showing the heart rate monitoring apparatus as the biological information measuring apparatus according to Embodiment 2.

The heart rate monitoring apparatus 1020 as the biological information measuring apparatus according to Embodiment 2 is installed on the subject's arm with a fixture part such as a band, as in the above Embodiment 1, though not shown in FIG. 15. On the inner side of the band (surface on the side of the subject's arm), groove parts similar to those of the above Embodiment 1 are provided. Since the groove parts thus provided improve ventilation between the skin and the outside, the subject's sweat and attached moisture can be released outside. Therefore, discomfort experienced by the subject due to the accumulation of drops of water can be reduced. The configuration of the groove parts is similar to that of Embodiment 1 and therefore will not be described further in detail here.

The heart rate monitoring apparatus 1020 as the biological information measuring apparatus according to Embodiment 2 has a sensor 1022 having at least two sensor elements (in this example, as three sensor elements, two light emitting elements 1221, 1223 as a first light emitting unit and a second light emitting unit, and a light receiving element 1222 as a light receiving unit, are used). The sensor elements detect sensor signals. The sensor 1022 has an optical sensor made up of light emitting elements 1221, 1223 using two LEDs for emitting light to the user's skin, and at least one light receiving element 1222 (photodiode) for receiving the light reflected from the skin. The heart rate monitoring apparatus 1020 also has a case or housing (not shown). The case or housing may be similar to or identical with the case 1014 shown in FIG. 14, or may be similar to or identical with the case unit 10 in the above Embodiment 1.

The sensor 1022 is carried on one surface of a carrier (substrate) 1026. The light emitted from the light emitting elements 1221, 1223 is reflected without being absorbed by the skin or the like and can directly reach the light receiving element 1222. In the heart rate monitoring apparatus 1020, the distance between the carrier 1026 and top surfaces 1221a, 1223a of the light emitting elements 1221, 1223 is shorter than the distance between the carrier 1026 and a top surface 1222a of the light receiving element 1222. That is, the difference between the distance between the carrier 1026 and the top surfaces 1221a, 1223a of the light emitting elements 1221, 1223 and the distance between the carrier 1026 and the top surface 1222a of the light receiving element 1222 is Δh. The light receiving element 1222 receives light on the top surface 1222a thereof, which is the outermost layer. These configurations have the effect that the majority of the light emitted from the light emitting elements 1221, 1223 travels toward the skin and that the reflected light becomes incident directly on the light receiving element 1222 without an air layer or the like in-between. In other words, since the light receiving element 1222 is structured to be in tight contact with the skin, a structure which makes it hard for a space to be generated between the top surface (light receiving surface) 1222a of the light receiving element 1222 can be provided and therefore light that becomes a noise source, such as external light, can be restrained from becoming incident on the top surface 1222a. Also, the light from the light emitting elements 1221, 1223 that is not transmitted through the skin, for example, the light becoming incident directly on the light receiving element 1222 from the light emitting elements 1221, 1223, cannot reach the top surface 1222a of the light receiving element 1222.

Embodiment 3

Figure 16:
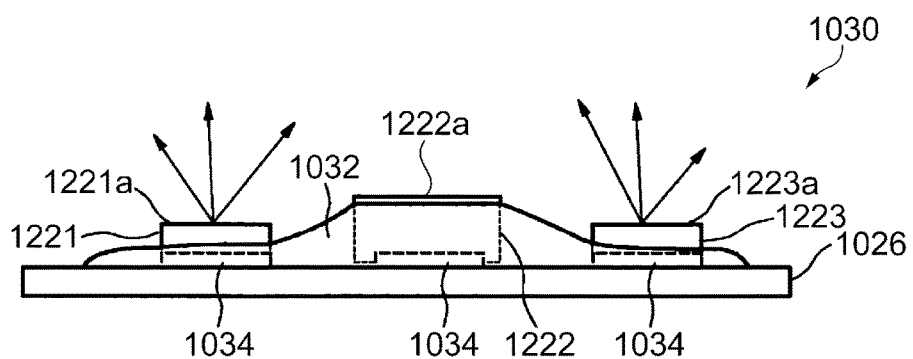
FIG. 16 is a front view showing a biological information measuring apparatus according to Embodiment 3.

Next, a heart rate monitoring apparatus 1030 as a biological information measuring apparatus according to Embodiment 3 will be described, referring to FIG. 16. FIG. 16 is a front view showing the heart rate monitoring apparatus as the biological information measuring apparatus according to Embodiment 3.

The heart rate monitoring apparatus 1030 as the biological information measuring apparatus according to Embodiment 3 is installed on the subject's arm with a fixture part such as a band, as in the above Embodiment 1, though not shown in FIG. 16. On the inner side of the band (surface on the side of the subject's arm), groove parts similar to those of the above Embodiment 1 are provided. Since the groove parts thus provided improve ventilation between the skin and the outside, the subject's sweat and attached moisture can be released outside. Therefore, discomfort experienced by the subject due to the accumulation of drops of water can be reduced. The configuration of the groove parts is similar to that of Embodiment 1 and therefore will not be described further in detail here.

As shown in FIG. 16, preferably, electrical connection terminals 1034 of light emitting elements 1221, 1223 and a light receiving element 1222 must be covered with an insulating material (for example, an epoxy resin) 1032 for protection of electrical elements. Alternatively, the insulating material 1032 can be formed not to cover the light emitting elements 1221, 1223 or the light receiving element 1222. Specifically, the insulating material 1032 can be formed to fill the area between the light emitting element 1221 and the light receiving element 1222 and the area between the light emitting element 1223 and the light receiving element 1222. In other words, the insulating material 1032 can be formed not to cover at least the top surface 1222a of the light receiving element 1222 or the top surfaces 1221a, 1223a of the light emitting elements 1221, 1223. With such a configuration, an obstruction due to an air gap between the skin and the light emitting elements 1221, 1223 can be restrained. Also, the insulating material 1032 may be formed to cover the top surfaces 1221a, 1223a of the light emitting elements 1221, 1223 and the top surface 1222a of the light receiving element 1222. With such a configuration, the top surface 1222a of the light receiving element 1222 that contacts the skin, and the top surfaces 1221a, 1223a of the light emitting elements 1221, 1223 can be protected. Therefore, damage to the top surface 1222a of the light receiving element 1222 and the top surfaces 1221a, 1223a of the light emitting elements 1221, 1223 can be prevented. In this case, the insulating material 1032 can be regarded as a protection film.

In the heart rate monitoring apparatus 1030 as the biological information measuring apparatus according to Embodiment 3, the insulating material 1032 using an epoxy resin is provided as a generally possible example. In FIG. 16, the insulating material 1032 is arranged without covering the top surfaces 1221a, 1223a of the light emitting elements 1221, 1223 and protects the electrical connection terminals 1034. The light emitted from the light emitting elements 1221, 1223 is indicated by arrows.

In this way, the insulating material 1032 is arranged to the minimum so as not to prevent correct functioning of the heart rate monitoring apparatus 1030. Thus, the electrical connection terminals 1034 of the light emitting elements 1221, 1223 and the light receiving element 1222 are protected, and the heart rate monitoring apparatus 1030 can be improved further. Instead of the configuration in Embodiment 3 in which the epoxy resin is injected, a heart rate monitoring apparatus 1040 as a biological information measuring apparatus according to Embodiment 4 as shown in FIG. 17 is more preferable.

Embodiment 4

Next, the heart rate monitoring apparatus 1040 as the biological information measuring apparatus according to Embodiment 4 will be described, referring to FIG. 17. FIG. 17 is a perspective view showing the heart rate monitoring apparatus as the biological information measuring apparatus according to Embodiment 4.

Figure 17:
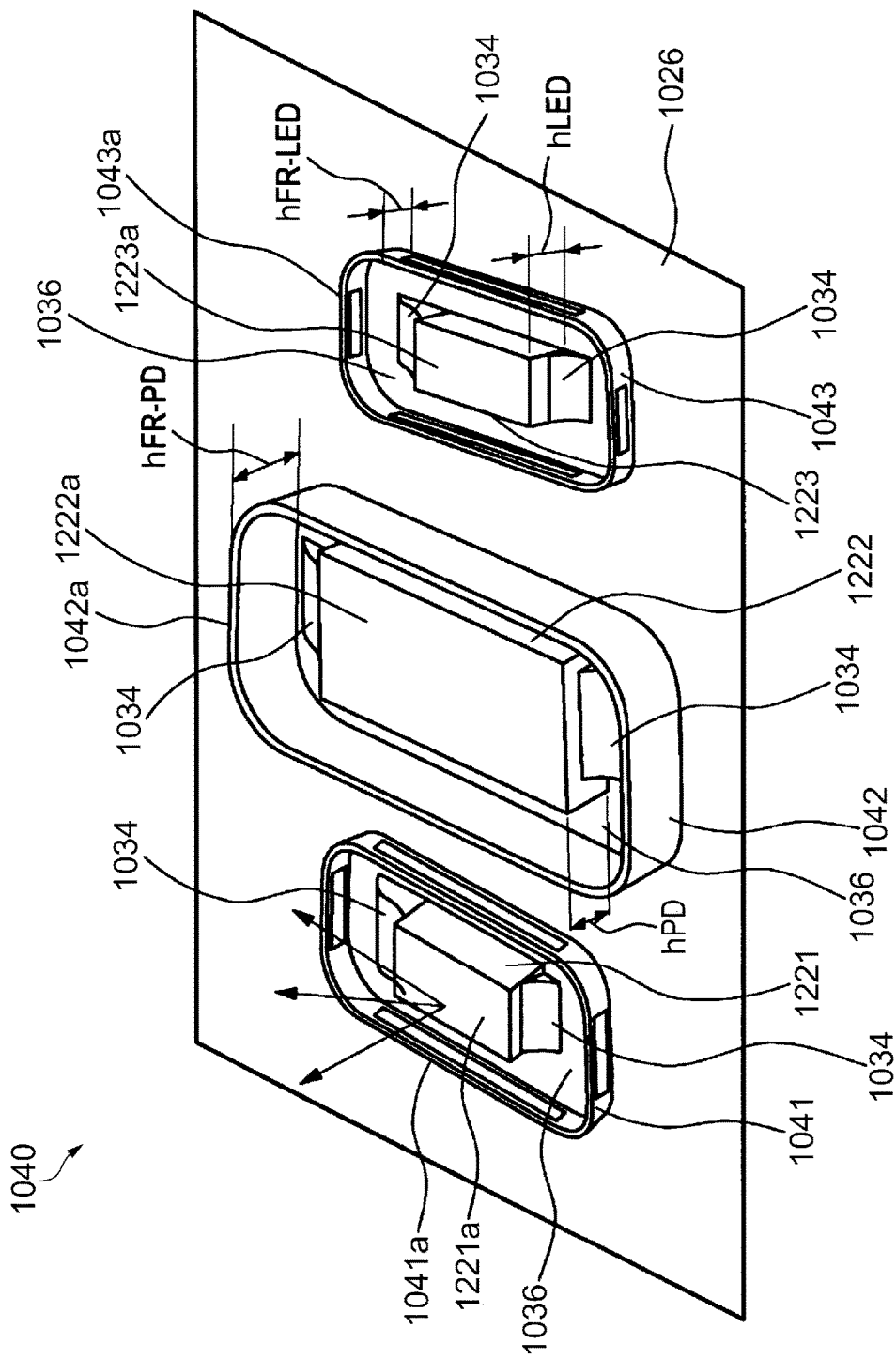
FIG. 17 is a perspective view showing a biological information measuring apparatus according to Embodiment 4.

The heart rate monitoring apparatus 1040 as the biological information measuring apparatus according to Embodiment 4 is installed on the subject's arm with a fixture part such as a band, as in the above Embodiment 1, though not shown in FIG. 17. On the inner side of the band (surface on the side of the subject's arm), groove parts similar to those of the above Embodiment 1 are provided. Since the groove parts thus provided improve ventilation between the skin and the outside, the subject's sweat and attached moisture can be released outside. Therefore, discomfort experienced by the subject due to the accumulation of drops of water can be reduced. The configuration of the groove parts is similar to that of Embodiment 1 and therefore will not be described further in detail here.

In the heart rate monitoring apparatus 1040 as the biological information measuring apparatus according to Embodiment 4, prepared frames 1041, 1042, 1043 are arranged. The frames 1041, 1042, 1043 are arranged around light emitting elements 1221, 1223 and a light receiving element 1222, thus forming spaces 1036 between the frames 1041, 1042, 1043, and the light emitting elements 1221, 1223 and the light receiving element 1222. An insulating material (not shown in FIG. 17) is injected with the frames 1041, 1042, 1043 used as guides, and covers electrical connection terminals 1034 of the light emitting elements 1221, 1223 and the light receiving element 1222.

In the example described in Embodiment 4, the light emitting elements 1221, 1223 and the light receiving element 1222 are surrounded by the frames 1041, 1042, 1043 corresponding to these elements. In another example, all of the frames 1041, 1042, 1043 may be connected together, or all of the sensor elements may be surrounded by a unified frame.

As an improvement in order not to affect the functionality of the heart rate monitoring apparatus 1040, it is preferable that top edges 1041a, 1043a of the frames 1041, 1043 around the light emitting elements 1221, 1223 are lower than top surfaces 1221a, 1223a of the light emitting elements 1221, 1223. In other words, the distance hFR-LED between the top edges 1041a, 1043a of the individual frames 1041, 1043 and a carrier 1026 is the same as or smaller than the distance hLED between the top surfaces 1221a, 1223a of the light emitting elements 1221, 1223 surrounded by the individual frames 1041, 1043 and the carrier 1026 (hFR-LED hLED).

Preferably, the difference between the distance hLED between the top surfaces 1221a, 1223a of the light emitting elements 1221, 1223 and the carrier 1026 and the distance hFR-LED between the top edges 1041a, 1043a of the frames 1041, 1043 and the carrier 1026 is set within the range from 0.1 mm to 0.8 mm. More preferably, the difference between the distance hLED between the top surfaces 1221a, 1223a of the light emitting elements 1221, 1223 and the carrier 1026 and the distance hFR-LED between the top edges 1041a, 1043a of the frames 1041, 1043 and the carrier 1026 is set within the range from 0.2 mm to 0.5 mm.

It is also preferable that a top edge 1042a of the frame (receiver frame) 1042 around the light receiving element 1222 is higher than a top surface 1222a of the light receiving element 1222. In other words, the distance hFR-PD between the top edge 1042a of the frame 1042 and the carrier 1026 is greater than the distance hPD between the top surface 1222a of the light receiving element 1222 surrounded by the frames 1042 and the carrier 1026 (hFR-PD>hPD).

Preferably, the difference between the distance hPD between the top surface 1222a of the light receiving element 1222 and the carrier 1026 and the distance hFR-PD between the top edge 1042a of the frame 1042 and the carrier 1026 is set within the range from 0 mm to 0.5 mm. More preferably, the difference between the distance hPD between the top surface 1222a of the light receiving element 1222 and the carrier 1026 and the distance hFR-PD between the top edge 1042a of the frame 1042 and the carrier 1026 is set within the range from 0.1 mm to 0.2 mm.

Moreover, the distance hFR-PD between the top edge 1042a of the frame 1042 and the carrier 1026 is greater than the distance hLED between the top surfaces 1221a, 1223a of the light emitting elements 1221, 1223 and the carrier 1026 (hFR-PD>hLED).

If, for example, the light receiving element 1222 and the light emitting elements 1221, 1223 are close to each other, a configuration in which only one frame wall exists between the light receiving element 1222 and the light emitting elements 1221, 1223 may be employed. This may take place for the reason of easiness of manufacturing. If the one frame wall is a case, the frame walls of the frames of both the light receiving element 1222 and the light emitting elements 1221, 1223 coincide with each other. This means that the frame walls of the light emitting elements 1221, 1223 are higher. Specifically, the frame walls on the side where the light receiving element 1222 is present, of the frames 1041, 1043 surrounding the light emitting elements 1221, 1223, are higher, and the other frame walls are lower than the top surfaces 1221a, 1223a of the light emitting elements 1221, 1223.

Also, instead of the frames 1041, 1042, 1043, a first wall part may be provided between the light receiving element 1222 and the light emitting element 1221 or the light emitting element 1223, and a second wall part may be provided on the outer side of the light emitting elements 1221, 1223, that is, the side opposite to the first wall part with respect to the light receiving element 1222.

In the case of such a configuration, the distance between the carrier 1026 and the top surface of the first wall part may be greater than the distance between the carrier 1026 and the top surface of the second wall part. With such a configuration, the functions of frames can be realized with fewer members than in the case where the light emitting elements and the light receiving element are surrounded as shown in FIG. 17.

With the use of the frames 1041, 1043 and the frame 1042 as in Embodiment 4, the insulating material injected there such as an epoxy resin can be prevented from flowing out. Also, preparing an additional structure to partition the insulating material such as an epoxy resin is an option that enables high productivity. The frames 1041, 1043 and the frame 1042 may be made of the same material of the carrier 1026. For example, the frames may be formed by injection molding with an epoxy-based resin or polycarbonate-based resin.

As described above, the insulating material 1032 (see FIG. 16) protects the electrical connection terminals 1034 of the sensor elements (light emitting elements 1221, 1223 and light receiving element 1222). However, the electrical connection terminals 1034 must further contact additional electronic devices as other elements (for example, a driver, detection electronics, processor, or power supply). It means that there is a certain electrical connection with the additional electronic devices, in the carrier 1026 (which may be a printed board (PCB)).

Embodiment 5

Figure 18:
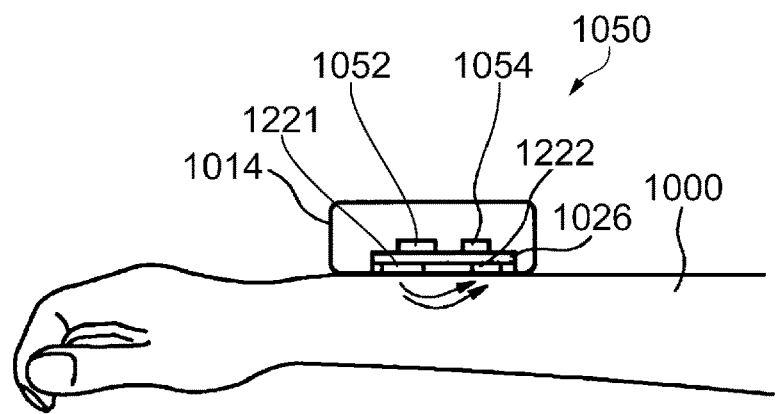
FIG. 18 is a cross-sectional view showing a biological information measuring apparatus according to Embodiment 5.

A heart rate monitoring apparatus 1050 as a biological information measuring apparatus according to Embodiment 5 will be described, referring to FIG. 18. FIG. 18 is a cross-sectional view showing the heart rate monitoring apparatus as the biological information measuring apparatus according to Embodiment 5.

The heart rate monitoring apparatus 1050 as the biological information measuring apparatus according to Embodiment 5 is installed on the subject's arm with a fixture part such as a band, as in the above Embodiment 1, though not shown in FIG. 18. On the inner side of the band (surface on the side of the subject's arm), groove parts similar to those of the above Embodiment 1 are provided. Since the groove parts thus provided improve ventilation between the skin and the outside, the subject's sweat and attached moisture can be released outside. Therefore, discomfort experienced by the subject due to the accumulation of drops of water can be reduced. The configuration of the groove parts is similar to that of Embodiment 1 and therefore will not be described further in detail here.

The heart rate monitoring apparatus 1050 as the biological information measuring apparatus according to Embodiment 5 has additional electronic devices as described above (for example, processor 1052 and driver 1054). An external electrical connection terminal (not shown) is not arranged on the same carrier 1026 as sensor elements (light emitting element 1221 and light receiving element 1222). That is, the additional electronic devices are arranged on a carrier or substrate that is different from the carrier of the sensor elements. With such a configuration, the necessary additional electronic devices can be installed in the heart rate monitoring apparatus 1050 while good contact between the skin and the sensor elements (light emitting element 1221 and light receiving element 1222) is maintained. For example, the external electrical connection terminal can be arranged on a lateral side of the carrier 1026.

As described above, it is possible to use different types of sensor in the biological information measuring apparatus according to the invention. For example, if the light receiving element 1222 is an electric sensor, two skin conductance electrodes (for example, sensor elements (the light emitting element 1221 and the light receiving element 1222 shown in FIG. 15)) which contact the user's skin for measuring the conductivity of the user are covered with the skin. Also, two or more additional types of sensors can be used in a biological information measuring apparatus of this type. Moreover, the number of sensor elements used is not particularly limited.

Figure 19:
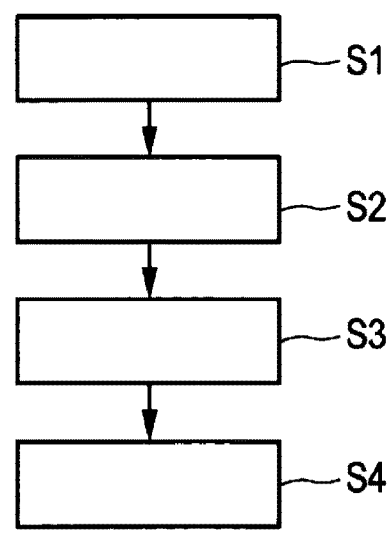
FIG. 19 is a flowchart showing a method for manufacturing the biological information measuring apparatuses according to Embodiments 2 to 5.

A flowchart of a method for manufacturing the biological information measuring apparatus which measures physiological parameters, proposed in Embodiments 2 to 5, is shown in FIG. 19.

In a first step S1, a sensor 1022 made up of at least two sensor elements (light emitting element 1221 and light receiving element 1222) for detecting a sensor signal is arranged on a carrier 1026. In a second step S2, an electrical contact of the sensor elements is formed in the carrier 1026. In a third step S3, one or more frames 1041, 1042 are formed on the carrier 1026, in the peripheries of the sensor 1022 and/or the individual sensor elements (light emitting element 1221 and light receiving element 1222). In a fourth step S4, an insulating material 1032 is injected in and fills the areas surrounded by the individual frames 1041, 1042 and not covering top surfaces 1221a, 1222a of the sensor elements (light emitting element 1221 and light receiving element 1222) provided on the carrier 1026.

According to the above Embodiments 2 to 5, a method that achieves the protection of the electrical contact without negatively affecting the performance of the biological information measuring apparatus is proposed. The protection is formed by a method that maintains the performance of the sensor. For example, at least one of the frames 1041, 1043 prevents the overall position of the sensor on the skin from shifting. Moreover, at least one of the frames 1041, 1043 can be useful in preventing directly emitted light from entering the light receiving element 1222. Preferably, the height of the frames 1041, 1043 around the light emitting elements 1221, 1223 on the side facing the light receiving element 1222 must be smaller than the height of the top surfaces 1221a, 1223a of the light emitting elements 1221, 1223. Moreover, the frame 1042 around the light receiving element 1222 may be higher than the top surface 1222a of the light receiving element 1222.

What is claimed is:

1. A biological information measuring apparatus comprising:
   a detection unit which detects biological information;
   a case unit which houses the detection unit; and
   a band which fixes the case unit to a living body;
   wherein the band is provided with a recessed groove part on a side facing the living body, and
   the groove part has a depth of 1020 μm or more and 1140 μm or less.

2. The biological information measuring apparatus according to claim 1, wherein the depth of the groove part is 1050 μm or more and 1100 μm or less.

3. The biological information measuring apparatus according to claim 1, wherein the depth of the groove part is 1060 μm or more and 1080 μm or less.

4. The biological information measuring apparatus according to claim 1, wherein the depth of the groove part at an end of the band is deeper than the depth of the groove part in the other parts of band.

5. The biological information measuring apparatus according to claim 1, wherein the groove part is provided along a direction of extension of the band.

6. The biological information measuring apparatus according to claim 5, wherein the groove part is provided to reach the case unit.

7. The biological information measuring apparatus according to claim 1, wherein the groove part is provided along a direction intersecting with a direction of extension of the band.

8. The biological information measuring apparatus according to claim 1, wherein the band has a hole part penetrating the band from the side facing the living body to the opposite side, and
the groove part is provided to continue to the hold part.

9. The biological information measuring apparatus according to claim 1, wherein the band includes a first band part extending on one side of the case unit, and a second band part extending on the opposite side via the case unit, and
the groove part is provided on the first band part and the second band part.

10. The biological information measuring apparatus according to claim 1, wherein the band is made of a material that is deformable along the living body.

11. The biological information measuring apparatus according to claim 10, wherein the band is made of an elastic resin material.

12. The biological information measuring apparatus according to claim 1, wherein the band includes a first band and a second band, the first band including the groove part and a buckle comprised with a flame and a buckle tongue, and the second band includes a plurality of holes to be inserted by the buckle tongue.

13. A biological information measuring apparatus comprising:
a detection unit which detects biological information;
a case unit which houses the detection unit; and
a band which fixes the case unit to a living body;
wherein the band is provided with a recessed groove part on a side facing the living body, and
the groove part has a width of 910 μm or more and 2300 μm or less.

14. The biological information measuring apparatus according to claim 13, wherein the width of the groove part is 950 μm or more and 2000 μm or less.

15. The biological information measuring apparatus according to claim 13, wherein the width of the groove part is 1000 μm or more and 1700 μm or less.

16. The biological information measuring apparatus according to claim 13, wherein the width of the groove part at an end of the band is broader than the width of the groove part in the other parts of the band.

17. The biological information measuring apparatus according to claim 13, wherein the band includes a first band and a second band, the first band including the groove part and a buckle comprised with a flame and a buckle tongue, and the second band includes a plurality of holes to be inserted by the buckle tongue.

* * * * *